(12) United States Patent
Sfinarolakis-Kokolis et al.

(10) Patent No.: US 12,569,190 B2
(45) Date of Patent: Mar. 10, 2026

(54) METHOD FOR MEASUREMENT OF VASCULAR ENDOTHELIAL RESPONSE TO STIMULI

(71) Applicants: Maria Sfinarolakis-Kokolis, Brooklyn, NY (US); Spyros Kokolis, Brooklyn, NY (US)

(72) Inventors: Maria Sfinarolakis-Kokolis, Brooklyn, NY (US); Spyros Kokolis, Brooklyn, NY (US)

( * ) Notice: Subject to any disclaimer, the term of this patent is extended or adjusted under 35 U.S.C. 154(b) by 684 days.

(21) Appl. No.: 17/744,280

(22) Filed: May 13, 2022

(65) Prior Publication Data

US 2023/0363706 A1 Nov. 16, 2023

(51) Int. Cl.
| | |
|---|---|
| *A61B 5/00* | (2006.01) |
| *G16H 40/63* | (2018.01) |
| *G16H 50/20* | (2018.01) |

(52) U.S. Cl.
CPC .......... *A61B 5/4839* (2013.01); *A61B 5/0022* (2013.01); *A61B 5/6802* (2013.01); *A61B 5/7264* (2013.01); *G16H 40/63* (2018.01); *G16H 50/20* (2018.01)

(58) Field of Classification Search
CPC ... A61B 5/4839; A61B 5/0022; A61B 5/6802; A61B 5/7264; G16H 50/20; G16H 40/63
See application file for complete search history.

(56) References Cited

U.S. PATENT DOCUMENTS

| | | | |
|---|---|---|---|
| 4,109,643 A | 8/1978 | Bond | |
| 4,241,738 A | 12/1980 | Lubbers | |
| 4,798,464 A | 1/1989 | Boostrom | |
| 5,043,571 A | 8/1991 | Hasegawa | |
| 5,297,555 A | 3/1994 | Martens | |
| 5,402,778 A | 4/1995 | Chance | |
| 5,564,417 A | 10/1996 | Chance | |
| 5,671,735 A | 9/1997 | MacFarlane et al. | |
| 6,011,985 A | 1/2000 | Athan | |

(Continued)

OTHER PUBLICATIONS

Furchgott, Robert F., The Nature of the Endothelium-Derived Relaxing Factor, www.hscbklyn.edu.

(Continued)

*Primary Examiner* — Alex M Valvis
*Assistant Examiner* — Jonathan M Haney
(74) *Attorney, Agent, or Firm* — Knobbe Martens Olson and Bear, LLP

(57) ABSTRACT

A method for evaluating the response of the vascular endothelium of a human subject to a stimulus, by observing the reaction of the endothelium before and after the topical application of a vasoactive substance, before and after application of the stimulus. The observation is carried out by at least one camera device, which may be a high-resolution spectrophotometric, THz, infrared, ultraviolet optical coherence tomography, or optical elasticity camera, which device is used to observe a skin area or areas of the subject. One device may take the measurements of the area of skin before and after topical application of a vasocative substance, or two devices may be used contemporaneously to each measure an area of skin with and without the topical substance. The device may be applied to the skin, or remote from the skin, or implanted in or under the skin.

15 Claims, 16 Drawing Sheets

(56) References Cited

U.S. PATENT DOCUMENTS

| | | | |
|---|---|---|---|
| 6,076,010 | A | 6/2000 | Boas |
| 6,132,380 | A | 10/2000 | Cohen |
| 6,437,866 | B1 | 8/2002 | Flynn |
| 6,993,167 | B1 | 1/2006 | Skladnev |
| 6,997,882 | B1 | 2/2006 | Parker |
| 7,008,350 | B1 | 3/2006 | Yamazaki |
| 7,483,733 | B2 | 1/2009 | Shani |
| 7,620,212 | B1 | 11/2009 | Allen et al. |
| 8,082,015 | B2 | 12/2011 | Yodh |
| 8,208,997 | B2 | 6/2012 | Nilsson |
| 8,236,516 | B2 | 8/2012 | Evelegh |
| 8,712,491 | B2 | 4/2014 | Evelegh |
| 8,948,832 | B2 | 2/2015 | Hong |
| 9,113,832 | B2 | 8/2015 | Al-Ali |
| 10,154,813 | B1* | 12/2018 | Kokolis ............... A61B 5/4848 |
| 10,835,126 | B1* | 11/2020 | Cong ................... A61B 5/0075 |
| 2004/0044080 | A1 | 3/2004 | Place |
| 2008/0214434 | A1 | 9/2008 | Stroes |
| 2011/0106201 | A1 | 5/2011 | Bhunia |
| 2013/0174077 | A1* | 7/2013 | Asami .................... A61B 5/744 |
| | | | 715/771 |
| 2014/0378779 | A1 | 12/2014 | Freeman |
| 2015/0335288 | A1 | 11/2015 | Toth |
| 2016/0073886 | A1 | 3/2016 | Connor |
| 2017/0000355 | A1 | 1/2017 | Lenehan et al. |
| 2017/0035514 | A1* | 2/2017 | Fox ........................ G06Q 10/10 |
| 2021/0345942 | A1* | 11/2021 | Kinsler ..................... G06T 7/50 |
| 2022/0240779 | A1* | 8/2022 | Peyman ............... A61B 5/0066 |

OTHER PUBLICATIONS

Furchgott, Robert F., Endothelium-Derived Relaxing Factor: Discovery, Early Studies, and Identification as Nitric Oxide, Noble Lecture—Health Science Center, Brooklyn, NY, Dec. 8, 1998.

Topical Non-Iontophoretic Application of Acetylcholine and Nitroglycerin via a Translucent Patch: A New Means for Assessing Microvascular Reactivity by Robert B. Schonberger et al. pub. Yale Journal of Biology and Medicine 79 (2006), pp. 1-7.

Bruce protocol by Wikipedia, pub. on line on Jan. 16, 2017 at <https://en.wikipedia.org/w/index.php?title=Bruce_protocol&oldid=760437118>.

Pulse oximetry by Wikipedia, pub. on line on Jun. 2, 2016 at <https://en.wikipedia.org/w/index.php?title=Pulse_oximetry&oldid=723407047>.

Aline J.Waclawovsky et al., Endothelial dysfunction in people with depressive disorders: A systematic review and meta-analysis (Abstract), Journal of Psychiatric Research vol. 141, Sep. 2021, pp. 152-159.

PJ Smith et al., Microvascular Endothelial Function and Neurocognition among Adults with Major Depressive Disorder, Am J Geriatr Psychiatry. Oct. 2018; 26(10): 1061-1069.

Morteza Naghavi et al., High Frequency of Microvascular Dysfunction in US Outpatient Clinics: A Sign of High Residual Risk? Data from 7,105 Patients, International Journal of Vascular Medicine vol. 2022.

L. Themstrup et al., Validation of Dynamic optical coherence tomography for non-invasive, in vivo microcirculation maging of the skin (Abstract), Microvascular Research, vol. 107, Sep. 2016, pp. 97-105.

Fernando Zvietcovich et al., Reverberant 3D optical coherence elastography maps the elasticity of individual corneal layers, Nature Communications | https://doi.org/10.1038/s41467-019-12803-4.

De Moraes et al. "Effects of non-supervised low intensity aerobic excise training on the microvascular endothelial function of patients with type 1 diabetes: a nonpharmacological interventional study", Springer research article, 2016.

Beck et al. "Exercise training improves endothelial function in young prehypertensives", Exp Biol Med (Maywood). Author manuscript; available in PMC 2015.

International Search Report and Written Opinion for PCT/US23/21839 dated Aug. 9, 2023 (OEE Work Product for accompanying PPH Request).

* cited by examiner

METHOD FOR MEASUREMENT OF VASCULAR ENDOTHELIAL RESPONSE TO STIMULI

FIELD AND BACKGROUND OF THE SUBJECT TECHNOLOGY

The subject technology relates to systems and methods for diagnosis of cardiac and vascular conditions, and for other medical purposes, by provoking and measuring the reaction of vascular endothelium to certain stimuli.

The vascular endothelium is the inner cellular lining of blood vessels, including arteries, capillaries, and veins. It is a layer of specialized cells, i.e. endothelial cells, between the blood and other tissues. The vascular endothelium is different (i.e. heterogeneous) in different parts of the vascular tree.

The vascular endothelium is a responsive organ which controls local conditions of the vasculature including the degree of vascular tone, constriction and/or relaxation, in response to certain physical, biochemical, and environmental stimuli. The endothelium performs many important homeostatic functions by regulating various humoral, neural and mechanical stimuli by releasing both contracting and relaxing signals that affect the underlying smooth muscle and vascular tone. Thus, by the control of vascular tone (and other mechanisms), endothelial cells (together with vascular smooth muscle tissue) regulate the blood flow to tissues and play a key role in maintaining cardiovascular homeostasis.

Vasoconstriction or vasodilation by action of the endothelial cells can be provoked by various local and systemic mechanisms. Vasoconstriction may result from local mechanisms including an increase in the partial pressure of oxygen (pO2), decrease of local temperature, and the presence of high concentration of adrenalin. Vasoconstriction may also result from systemic mechanisms including the presence in blood plasma of agents including angiotensin II, vasopressin, serotonin, endothelin A, thromboxane A2, and other factors. Vasodilation may result from local mechanisms including a decrease in pO2, an increase in nitric oxide (NO), potassium cation, hydrogen cation, hydrogen sulfide and/or local temperature, additionally, low concentration of adrenalin. Vasodilation may result from systemic mechanisms including the presence in blood plasma of agents including endothelin B, bradykinin, kallikrein, histamine, and serotonin.

Vasoconstriction or vasodilation of blood vessels in or near enough the skin may be induced by the application of topical vasoactive agents, for example but not limited to, bradykinin, dobutamine, dopamine, epinephrine, norepinephrine, substance p, vasopressin, milrinone, beta blockers, calcium channel blockers, angiotensin receptor blockers, ACE inhibitors, phenylephrine, levosimendan, nitroprusside, nesiritide, isoprotenol, nitroglycerin, nitric oxide, citrulline, serotonin, adenosine, acetylcholine, arginine, guanylate cyclase inhibitors, endothelin antagonists, prostaglandins, phosphodiesterase inhibitors, ultraviolet light and infrared light. The skin is particularly suited to respond to exposure to these substances with the vast capillary networks that supports its function. The capillaries, rich in endothelial cells, react instantly to any foreign chemical or physiological stimulus. Vasoconstriction or vasodilation of blood vessels may also be induced by systemic factors (such as exercise, tobacco smoking) and environmental factors (heat or cold) and chemical stimuli and varying concentrations of bioavailable gases in the bloodstream such as; $NO_2$, $PO_2$, $PCO_2$, etc.

The vascular endothelium and its response to stimuli may be implicated in, or affected by, pathophysiological process including cardiac and cardiovascular diseases, hypertension, diabetes mellitus, atherosclerosis, infection, inflammatory illness, ischemia and vascular insufficiency. These disease processes may be present even in young persons and may be difficult to diagnose before serious damage has been done, which may be irreversible or require medicinal or surgical intervention. Evaluation and optimization of endothelial function may help preserve a person's long term cardiac health and well being.

Certain systems and methods of monitoring the functioning of the vascular endothelium are known. Endothelial function can be ascertained during cardiac catheterization procedures utilizing fractional flow reserve computation by passing pressure flow wires into arteries and measuring pressures before and after select areas in the arteries. This technique requires a catheterization laboratory and operating room set and it takes about 25 minutes to obtain a result and requires specialized equipment and skilled personnel to perform. The other methodology currently used is the VENDYS® system, which performs non-invasive testing of vascular reactivity using occlusion of arteries and measuring temperature differences. This non-invasive procedure can be done in an outpatient environment like a clinic and results are obtained in about an hour.

Methods and apparatus for patent skin color monitoring and drug efficacy measurement are also the subjects co-invented and co-owned U.S. Pat. Nos. 10,123,738 and 10,154,813, the entire disclosures of which are incorporated herein by reference.

BRIEF SUMMARY OF THE SUBJECT TECHNOLOGY

The subject technology relates to systems and methods for rapid, continuous, real-time or near-real-time monitoring and measuring of the response of vascular endothelium to certain stimuli including the application of vasoactive agents. The resulting information has numerous medical applications including diagnosis of disease, medication management, titration of pharmacotherapy, and assessment of exercise routines, among other applications. These medical applications, more specifically, include assisting in medication management and/or titration of pharmacotherapy in the field of psychiatric medication, for example, administration of lithium salts, antidepressants, and other such interventions.

The subject technology includes using an imaging device (for example, a color digital camera) which captures a first images of an observed area of a subject's skin. The image is analyzed to detect the state of the vascular endothelium in the observed area. The vascular endothelium of the subject is stimulated with vasoactive, vasoconstrictive, and/or vasodilative stimuli, and second images of the observed area are captured and analyzed with respect to the first images.

In embodiments of the subject technology, a pair of devices, e.g. high-resolution spectrophotometric cameras, or THz cameras, or infrared cameras, or ultraviolet cameras, or HSV, or OCT, OCE, or video computer analogue cameras are used to observe a skin area of the subject. One device reads baseline values (without a vasoactive substance applied) and the other reads with values vasoactive compound applied, i.e., the devices take before and after readings (and, optionally, continuous readings and recordings) of select vascular areas of the skin, oral and buccal, rectal, or vaginal mucosa to assess the endothelial function with physical exertion, pre- and post-image acquisition with devices described above, with and then without the medicinal compound. Readings are yielded within seconds of the onset of testing with minimal training and can be conducted on a subject or on oneself in any environment or situation.

In a non-limiting embodiment of the subject technology, in which a single color photography device is used sequentially for the dry run and wet run, a method for evaluating the response of the vascular endothelium of a human subject to a stimulus comprises the steps of: a) determining at least one baseline value of a first observed area of the subject's skin by photographing the first observed area with a first color photography device before any application of a vasoactive substance in the first observed area, the first color photography device being a spectrophotometric camera or digital color camera and not a colorimeter, the first color photography device outputting at least one first digital value in a color space, the at least one first digital value including at least one first red value of the color space, the at least one baseline value corresponding to the at least one first red value; b) applying the vasoactive substance topically to the first observed area; c) determining at least one vasoactivated value of the first observed area by photographing the first observed area with the first color photography device after applying the vasoactive substance topically to the first observed area, the first color photography device outputting a second digital value in the color space, the second digital value including at least a second red value of the color space, the at least one vasoactivated value corresponding to the at least a second red value; d) comparing the at least one vasoactivated value with the at least one baseline value to determine the response of the vascular endothelium of the human subject prior to applying the stimulus; e) applying the stimulus to the human subject; f) repeating steps (a)-(c); g) comparing the at least one vasoactivated value from step (f) with the at least one baseline value from step (f) (i.e. the post-stimulus test results) to determine the response of the vascular endothelium of the human subject to the stimulus.

In a non-limiting embodiment of the subject technology, in which two color photography devices are used contemporaneously for the dry run and wet run, a method for evaluating the response of the vascular endothelium of a human subject to a stimulus comprises the steps of: a) determining at least one baseline value of a first observed area of the subject's skin by photographing a first observed area with a first color photography device without any application of a vasoactive substance in the first observed area, the first color photography device being a spectrophotometric camera or digital color camera and not a colorimeter, the first color photography device outputting at least one first digital value in a color space, the at least one first digital value including at least one first red value of the color space, the at least one baseline value corresponding to the at least one first red value; b) contemporaneously with step (a), determining at least one vasoactivated value of a second observed area to which a vasoactive substance has been topically applied, by photographing the second observed area with a second color photography device, the second color photography device outputting a second digital value in the color space, the second digital value including at least a second red value of the color space, the at least one vasoactivated value corresponding to the at least a second red value; c) comparing the at least one vasoactivated value with the at least one baseline value to determine the response of the vascular endothelium of the human subject prior to applying the stimulus; d) applying the stimulus to the human subject; e) repeating steps (a) and (b); f) comparing the at least one vasoactivated value from step (e) with the at least one baseline value from step (e) (i.e. the post-stimulus test results) to determine the response of the vascular endothelium of the human subject to the stimulus.

In a non-limiting embodiment of the subject technology, in which a single vasculature imaging device is used sequentially for the dry run and wet run, a method for evaluating the response of the vascular endothelium of a human subject to a stimulus comprises the steps of: a) determining at least one baseline value of a first observed area of the subject's skin by digitally imaging vasculature in the first observed area with a first imaging device prior to any application of a vasoactive substance in the first observed area, the first imaging device being a terahertz camera, infrared camera, ultraviolet camera, optical coherence tomography (OCT) camera, or optical coherence elasticity (OCE) camera, and not a colorimeter, the first imaging device outputting at least one first digital image of the vasculature, the at least one baseline value corresponding to the at least one first digital image; b) applying the vasoactive substance topically to the first observed area; c) determining at least one vasoactivated value of the first observed area by digitally imaging vasculature in the first observed area with the first imaging device, the first imaging device outputting at least one second digital image of the vasculature, the at least one vasoactivated value corresponding to the at least one second digital image; d) comparing the at least one vasoactivated value with the at least one baseline value to determine the response of the vascular endothelium of the human subject prior to the stimulus. e) applying the stimulus to the human subject; f) repeating steps (a)-(c); g) comparing the at least one vasoactivated value from step (f) with the at least one baseline value from step (f) (i.e., the post-stimulus test results) to determine the response of the vascular endothelium of the human subject to the stimulus.

In a non-limiting embodiment of the subject technology, in which two vascular imaging devices are used contemporaneously for the dry run and wet run, a method for evaluating the response of the vascular endothelium of a human subject to a stimulus comprises the steps of: a) determining at least one baseline value of a first observed area of the subject's skin by digitally imaging vasculature in the first observed area with a first imaging device without any application of a vasoactive substance in the first observed area, the first imaging device being a terahertz camera, infrared camera, ultraviolet camera, optical coherence tomography (OCT) camera, or optical coherence elasticity (OCE) camera, and not a colorimeter, the first imaging device outputting at least one first digital image of the vasculature, the at least one baseline value corresponding to the at least one first digital image; b) contemporaneously with step (a), determining at least one vasoactivated value of a second observed area to which a vasoactive substance has been topically applied, by digitally imaging vasculature in the second observed area with a second imaging device, the second imaging device being a terahertz camera, infrared camera, ultraviolet camera, optical coherence tomography (OCT) camera, or optical coherence elasticity (OCE) camera, and not a colorimeter, the first imaging device outputting at least one second digital image of the vasculature, the at least one vasoactivated value corresponding to the at least one second digital image; c) comparing the at least one vasoactivated value with the at least one baseline value to determine the response of the vascular endothelium of the human subject prior to to the stimulus d) applying the stimulus to the human subject; e) repeating steps (a) and (b); f) comparing the at least one vasoactivated value from step (e) with the at least one baseline value from step (e) (i.e., the post-stimulus test results) to determine the response of the vascular endothelium of the human subject to the stimulus.

DETAILED DESCRIPTION OF THE SUBJECT TECHNOLOGY

Figure 1:
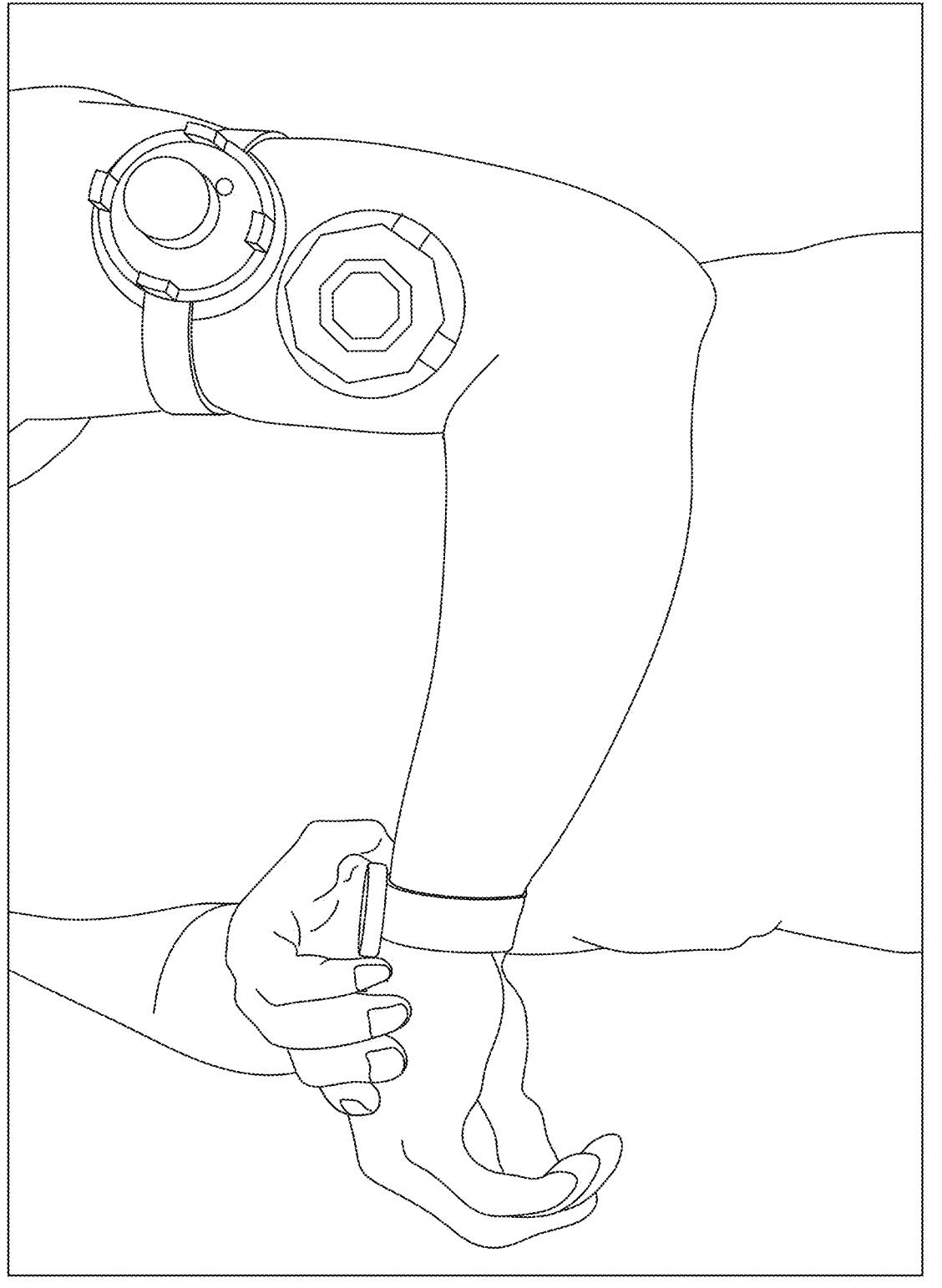
FIG. 1 is a photograph of subject wearing two imaging devices for evaluation of the subject's vascular endothelium according to a non-limiting embodiment of the subject technology.

The subject technology concerns systems and methods for rapid, real-time or near-real-time monitoring of the epithelial response to vasoactive stimuli, particularly as can be observed and measured via observation of the skin via camera systems. The skin's large surface area, and its extensive network of capillaries which are the peripheral ends of the same endothelial system that exists throughout the body provides testing sites which are exploited in the subject technology. More specifically, the quality of perfusion of capillary blood flow through the skin is measured and tested by the subject technology, which is essentially a test of the vasoreactivity of the endothelium. This vasoreactivity is the key to understanding the condition of the cardiovascular system. The subject technology is effectively a micro-vascular stress test of the endothelium which yields the most relevant cardiac information; endothelial reserves with stimulus, be it the effect of medication, stress, pregnancy, infection, exercise, etc. These parameters are key indicators of cardiac health and prior to the subject technology have been evasive to test. The results of the subject technology are prognostic indicators for multiple conditions such as asthma, chronic obstructive pulmonary disease, ischemic heart disease, heart hypercholesterolemia, congestive heart failure, diabetes, and hypertension, as well as monitoring the progress of exercise routines for medical or physical therapy. The subject technology may also be used to determine the efficacy in the subject of cholesterol medications, heart failure medications, blood thinning medications and blood pressure medications.

The observed area of the subject's skin may be selected from a variety of places on the body, including the face, cheeks, arms, legs, wrists, ankles, feet, hands, mucosa, rectum, vagina, or urethra. The variety of sites on the skin and skin types (oral or buccal, vaginal, urethral and or rectal) provide many opportunities to generate readings of skin reactivity, and receptivity. The skin of the core areas of the body, including the face and torso, are especially indicative of the health of the vascular system underlying the skin. However, the skin of peripheral areas, such as arms and legs, is also indicative and may be used as the observed area in embodiments of the subject technology.

The observed area of skin may be measured by a variety of imaging technologies, provided that the technologies are effective to measure the vasoreaction of the epithelium to the application of vasoactive substances. For example, in various embodiments, the imaging technologies are terahertz (THz), infrared (IR), ultraviolet (UV), RGB, Y CbCr, Hue, Saturation, Value (HSV), Optical Coherence Tomography (OCT), Optical Coherence Elasticity (OCE), EMF waves and or Lab spectrophotometric and colorimetric scan. In embodiments, the imaging device is a wearable device which is worn by the subject over the observed area. The wearable device may be incorporated into a wearable garment such as a sleeve, legging, mask, or similar garment, and may incorporate two or more imaging devices. In other embodiments, two imaging devices are used to observe two adjacent or nearby observed areas, a first area which has not been treated with a vasoactive substance, and a second area what has been treated with a vasoactive substance. In other embodiments, the color imaging device is a smartphone with a camera, the smartphone having an accessory attached which enables the smartphone camera to function as a spectrophotometer. In other embodiments, the imaging device is an implantable device which is implanted under the skin and records the color of the adjacent skin, similar in the manner and implementation of a loop recorder (also called a cardiac event recorder).

In other embodiments, an imaging device (e.g. a color camera system described above) is located near the subject but not in contact with the subject, and is in digital data communication with a server, optionally over a VPN (virtual private network) data connection, for data collection and analysis. This would allow to include the study of performance enhancers, psychoactive substances, stress hormones, lie detection and the effect of toxin exposure and bacterial or viral or parasitic infections, as well as various pharmacological medicinal exposure.

In embodiments of the subject technology, a digital image of the observed area of a subject is acquired by a smart device such as a smartphone, smart mirror and or other sensitive and specific photographic machine, and the image is digitally stored. The evaluation f the before and after treatment of the observed area with ultra-sensitive color differentiation software reveals a data shift in color that translates to degrees of endothelial response. This image measures the colorimetric and spectrophotometric analysis of the skin area, as described in a given color space (plotted in RGB, YCbCr or other color space). (It, should be understood that the subject technology is not limited to digital color photography, and that other digital imaging technologies may be utilized in embodiments, for example, terahertz reflective imaging and optical coherence tomography.) This initial image acquisition can be taken by the imaging device at varying distance from the observed skin area depending on the desired type of evaluation. Degrees of device proximity to the observed area yields different data sets that result in a comprehensive endothelial function value result. After acquisition of the initial "dry run" (no vasoactive substance administration) images, a vasoactive substance is applied by, for example aerosol spray, roll on, sprayed on and or rubbed on the observed area. The imaging device (or in some embodiments a second similar imaging device) then takes a digital image as in the "d run." The new is compared to the old image, and based on the variance and the algorithmic change from the "dr run" image to the "wet run" (with vasoactive substance administration) image in color space. The resulting data sets are plotted over time and the variance of change can be identified and plotted. The change can then be used to evaluate the patient progress over time to establish the effectiveness of medicinal treatments, physical therapy treatment and or the evaluation of a treatment from surgical or medical procedure for the patient.

Healthy endothelium will react to the vasoactive stimulus with a consistent and predictable (electromagnetic wave or particle alterations) red-shift or "A-shift" upon use of this process, while unhealthy endothelium has a dysfunctional (electromagnetic wave or particle alteration) red-shift and reveals vasoconstriction instead of vasodilation in the presence of vasoactive substances. This paradoxical result, defined as a negative red-shift or negative "A-shift," is an indication of heart disease and/or vascular insufficiency in the subject. The negative red-shift value may be observed with the subject technology in the sickest of patients as well as gradients of negative, zero, or slightly positive red-shift in those with mild to moderate disease, depending on the condition of the subject's vascular endothelium. The fittest and objectively healthiest subjects result in a robust positive red-shift with sustained vasodilation upon application of vasodilating compounds.

The digital image device may be, for example, a smartphone camera held from a small distance from the subject or from a more remote location that can evaluate a large area of the patient as they enter a particular room or area. Other electromagnetic or sound wave devices may be used. In all cases, there is an evaluation of the captured images before the application of the vasoactive substance and after, which differences can be plotted as a change over a time period, allowing for the evaluation of the endothelial functional change of the subject's skin in the observed area that has occurred over time.

These differences in the a-shift between wet and dry runs can be plotted different calculations such as $\Delta=\sqrt{(x_2-x_1)^2+(y_2-y_1)^2+(z_2-z_1)^2}$ or similar calculations used to calculate distance between points in a color sphere. These points are between the wet runs and dry runs.

Thus, the health monitoring system and method of the subject technology utilizes images of the body obtained by the use of spectrophotometer, colorimeter, smartphone high megapixel camera, terahertz reflective analysis, and/or optical coherence tomography; used individually and in concert depending on the data sets required. Additionally, readings can be obtained from multiple imaging modalities and be assessed by monitoring devices from closed circuit television recording devices from across the room or from imaging devices placed in mirrors or corners of rooms or any tele visual acquiring device. The images acquired will subsequently be analyzed and cataloged as data fields and tables used to tabulate the results of the testing information of the skin before and after exposure to a vasoactive substance that is applied and further changes in monitoring can be implemented.

The vasoactive substances and their application to the subject may take different forms in different embodiments. The vasoactive substances used in embodiments of the subject technology are comprised of a chemically heterogeneous group, proteins, peptides, lipids, and nucleosides, affecting vascular tone and leading to either vasodilation or vasoconstriction, the direction and magnitude of the reaction dependent on endothelial tone and function. A vasoactive compound may be applied to the skin via aerosolization, or by ingestion by oral route, subcutaneously, intravenously, rectally, or vaginally.

In an embodiment, the subject technology uses two highly sensitive colorimetric and spectrophotometric cameras directed at the subject that compare the baseline skin color value (without application of a vasoactive substance, i.e. "a dry run") and resultant color value of the skin's exposure to vasoactive substances, such as acetylcholine (i.e. a "wet run") or other vasoactive substance described above. Both the baseline color value and resultant color value are represented in a color space, for example the CIELAB color space.

Software linked to the cameras generates and translates the data to numerical values of color pixels captured by the imaging device or devices that can be charted over a specified time interval.

In an embodiment, a high-resolution color camera or spectrophotometric camera is used as the imaging device. By using high-resolution devices, the recognition of the pixels in given images is improved, so that the subject technology not only consider individual ranges of the three-color parameters of a color space, but also takes into account combinational ranges which provide greater accuracy in recognizing the imaged area.

In an embodiment using the CIELAB color space, the color space has three coordinates, specifically, lightness of the color L* (0 indicates black and 100 indicates white), its redness a* (negative values indicate greenness and positive values indicate redness) and blueness b* (negative values indicate blueness and positive values indicate yellowness). The change from the baseline (pre-stimulus) to resultant (post-stimulus) color values, although perhaps invisible to the naked eye, are measured by the imaging device, and gives an objective quantification of the "Red Shift" or "A-shift" which correlates directly to the quality of blood perfusion from the endothelium to the skin.

It should be understood that the use of other color spaces would be within the scope of the subject technology. By way of explanation, for example, in addition to the CIELAB color space, other color spaces are known, including the YCbCr and RGB color spaces. The difference between YCbCr and RGB is that YCbCr represents color as brightness and two-color difference signals, while RGB represents color as red, green and blue. In YCbCr, the Y is the brightness (luma), Cb is blue minus luma (B-Y) and Cr is red minus luma (R-Y). YCbCr is a known color space in digital video with MPEG compression, which is used for example in DVDs, digital TV, video CDs, and digital camcorders (MiniDV, DV, Digital Betacam, etc.), which output YCbCr encoded image data over a digital link such as FireWire or SDI. The ITU-R BT.601 international standard for digital video defines both YCbCr and RGB color spaces. These color spaces are all viable comparative values systems for rendering results from pre and post treatment data sets. Additionally, there is the HSV valuation system with the RGB overlay. The HSV color space (hue, saturation, value) is often used to determine colors (e.g., of paints or inks) from a color spheres or palettes, because of it correspondence to the RGB color space. The functions rgb2hsv and hsv2rgb convert images between the RGB and HSV color spaces using MATLAB. As hue varies from 0 to 360 degrees, the corresponding colors vary from red, through yellow, green, cyan, blue, and magenta, back to red, so that as saturation varies from 0 to 1.0, the corresponding colors (hues) vary from unsaturated (shades of gray) to fully saturated (no white component). As value, or brightness, varies from 0 to 1.0, the corresponding colors become increasingly brighter.

No matter which color space is being used in an embodiment, the results retrieved from the system may be plotted on a 2D graph; the x-axis being time and the y-axis being the color data measured by the camera(s) over time of the baseline color values and the resultant color values. During the evaluation subjects may be at rest or conducting physical activities like lifting weights or walking on a treadmill.

With respect to the application of a vasoactive substance to the subject's skin for the "wet run", in an embodiment, acetylcholine or other vasoactive substance is applied to the observed area of the subject's skin, via aerosolized spray or roll-on for example. After application of the substance, a video picture is again taken and acquired in the same digital video color space (e.g. CIELAB, RGB, YCbCr) by the same device, or a second device, and then the cameras can be used to again further acquire the data a few seconds to minutes after the initial values are obtained, so there is a data set with respect to time.

Considering an embodiment of the subject technology in which the YCbCr and HSV color spaces are being used, for example, the subject being evaluated is first photographed by a high-sensitivity digital color camera, which may be a still or video camera, prior to the application of any vasoactive substance to the skin. In this example, the skin color observed by the camera is Y=134, Cb=87, Cr=179 or H=330°, S=0.52, V=0.48. After application of a vasoactive substance, the same camera is used to again photograph the subject's skin, and in this example, the color observed is Y=128, Cb=75, Cr=189 or H=300°, S=0.43, V=0.69. The "red shift" thus measured is caused by the change in the perfusion of blood in the subject's skin due to the reaction of the epithelium to the vasoactive substance. The "red shift" may be calculated in the YCbCr color space in this example as: ImagePre YCbCr (Red)/ImagePost YCbCr (Red)=A in YCbCr (Red Color); ImagePre YCbCr (Blue)/ImagePost YCbCr (Blue)=A in YCbCr (Blue Color); ImagePre YCbCr (Y intensity)/ImagePost YCbCr (Y intensity)=A in YCbCr (Y intensity). Or, the "red shift" may be calculated in the HSV color space in this example as: ImagePre Hue/ImagePost Hue=A in Hue Color Histogram; ImagePre Saturation/ImagePost Saturation=A in Saturation Color Histogram; ImagePre Value/ImagePost Value=A in Value Color Histogram. The images between the wet and dry The color tone resulting from endothelial functions is varied for different subjects and from one region of a subject's skin to another region. The YCbCr color space is particularly well-suited for use in the subject technology and the required segmentation and detection of skin color in color images, which unlike the RGB color space, does not mix color (chrominance) and intensity (luminance) information and its non-uniform characteristics.

Evaluations may be performed on a given subject in various states or phases of treatment, for example, before and after a course of medicinal or therapeutic therapy. Multiple data points can be accumulated with respect to each individual subject that is then evaluated against their own previous results. Graphing these results over time (i.e., viewing the data as a time series) reveals the improvement or lack thereof of any medicinal or therapeutic treatments. The ability of the subject technology to achieve rapid results can ascertain which medication produces the best endothelial response according to their "A" shift. This can indicate necessary intervention by either medication implementation or exercise with or without physician assisted intervention and supervision. For example, the ability to determine which exercise produces the best enhancement of endothelial function running versus cycling or which statin is more beneficial or effective for the patient, Lipitor® versus Crestor®, as well as the appropriate dosing for the individual patient. This is an improvement over the "ALARA principle," i.e. "as low as reasonably achievable," currently used for monitoring serum cholesterol and low density lipoprotein values in cases of hypercholesterolemia. As of today, there is no test or protocol to know what is the appropriate dosage that can be implemented so rapidly and accurately as with the subject technology.

Figure 9:
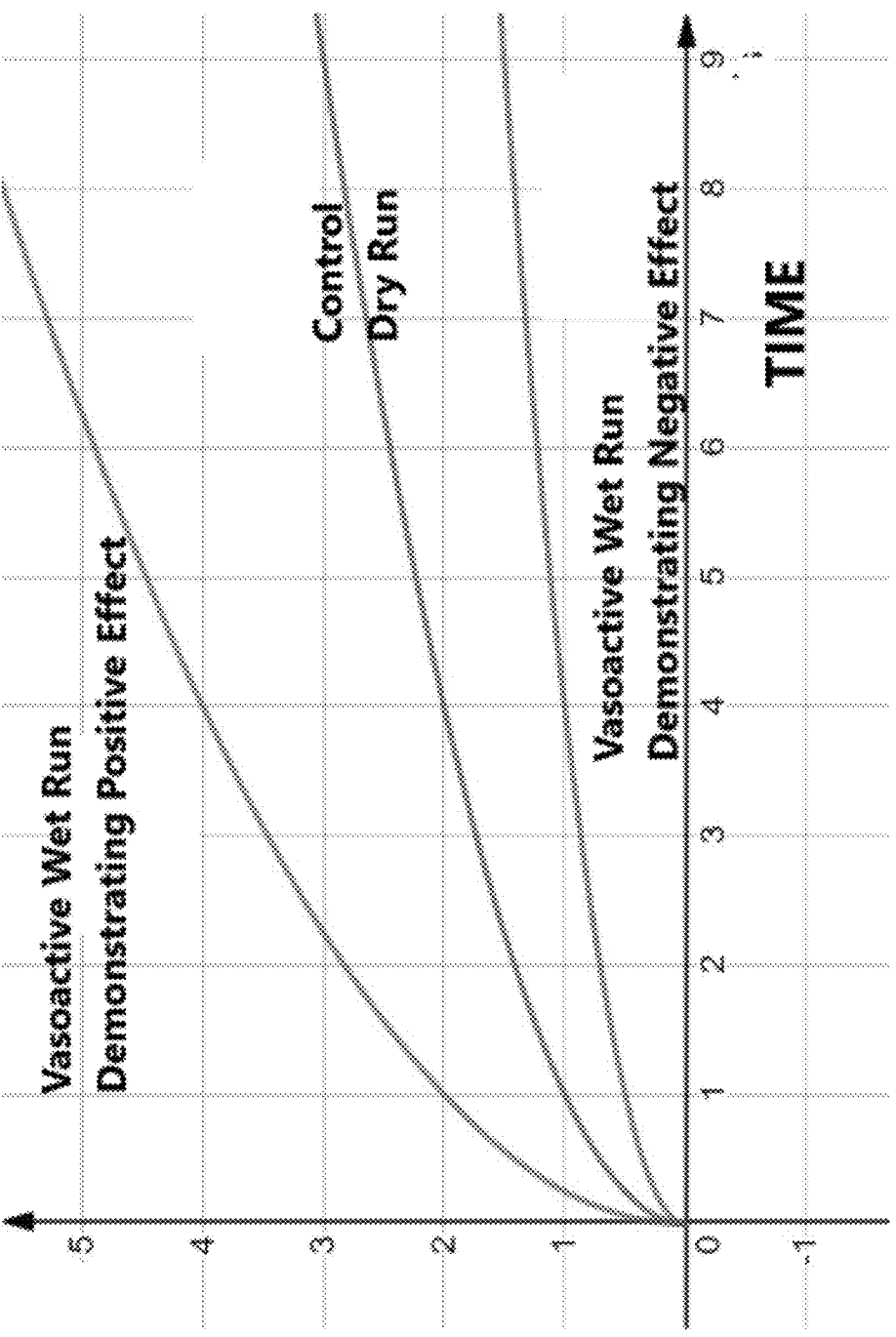
FIG. 9 is a time plot of exemplary data which is captured and analyzed in an embodiment of the subject technology.

FIG. 9 illustrates an example of plotted data according to the subject technology. The X-axis represents time, during which the subject may be physically exercising. The middle line represents the measured red color of the subject area during the control "dry run" over a period of time. The upper line represents a "wet run" of the same observed area, in this case, the epithelium is responding appropriately as in a healthy subject, indicated by the increase in measured red color of the observed area over time. The lower line represents a "wet run" of the same observed area, in this case, the epithelium is responding inappropriately as in an unhealthy subject, indicated by the decrease in measured red color of the observed area over time.

The subject technology is readily used in screening apparently healthy subjects, people at all ages and levels of fitness, for endothelial changes for cardiovascular conditions which may be asymptomatic or otherwise difficult to detect. Our default assumption is that all persons are healthy unless they have symptoms. This is the fallacy that will often prevent timely medical intervention. The subject technology is applicable to various degrees with which endothelial illness manifests prior to needing advanced intervention, and which varies greatly. Cases of young otherwise healthy seeming people experiencing sudden onset of symptoms and even death from cryptic heart conditions could be eradicated with a few moments of endothelial testing at a young age and in regular intervals throughout life. The subject technology may be used for endothelial evaluation at the onset of new exercise routines, new medications, sports injuries, pregnancy, admission to emergency room, emotional and physical stress, chronic illness diagnosis and therapeutic implementations, etc. The execution of the endothelial function values can generate a considerable knowledge of their appropriate homeostatic environment for anyone interested in improving their health and fitness.

As previously explained, the cameras according to the subject technology may be set up some distance from the subject. For example, in an embodiment, a camera system is set up a few feet from an entryway which people can pass through with a set light above them that would provide the appropriate lumens required that would allow for stable reproducible readings of the CIELAB a*b*L* values of the spectrophotometric/colorimetric camera and they would be immediately ascertained and used to compare to the same set of value data points that would again be taken with a similar system as before in terms of the light source, except the subjects would have the application of the vasoactive substance over their skin (i.e. the "wet run"). Thus, a system of the subject technology can be used in any setting to obtain data points for the individual that needs to be assessed for a variety of reasons that includes the health and wellness of the individual. Cameras may be set up, for example, as video camera systems that obtain digital information from a distance such as the placements in schools or airports or any closed circuit monitoring feeds that use both analogue systems with the YPbPr color space or the digital systems such as the RGB or YCbCr digital systems as well as the HSV color spaces and CIELAB. This will allow the spectrophotometric/colorimetric camera system to again take the readings of a*b*L* of CIELAB (for example) and plot these values against the prior data points without the vasoactive substance that was acquired a few moments before. This will allow the acquisition of multiple rapid accumulation of a*b*L data points pre and post vasoactive substance acquisition that can be used to evaluate the effects of the endothelial function in the persons undergoing the testing from a camera system that is across from them and not n direct contact with them. This will also allow for the vasoactive change elicited by the mechanisms caused by different stressful situations, for example exercise, drug comparisons, exercise, lie detection, fertility level and this can then allow the observing individual to make determinations of the subject's cardiovascular state and efficacy of different stimuli of exposure.

In a further aspect of the subject technology, the system of the subject technology may be programmed and configured to measure the skin color, and the change in skin color after application of a vasoactive substance, at a pre-determined location on the subject's body, using an imaging device located at a distance from the subject. It should be understood that a camera photographing a subject from a distance will capture an image including an extended area of the subject (for example, the entire face) along with clothing, background, and other objects. In an embodiment, the system of the subject technology may be programmed and configured to perform biometric facial recognition, as is known in the digital photography and videography art, and to locate within the digital picture, a given location with respect to facial landmarks, and measure the skin color and change of skin color at that given location.

For example, in an embodiment of the subject technology, it is advantageous to measure the skin color at the area of the frontal sinuses, located between the eyes and above the nose (i.e., that is the "observed area" of the skin), because of the size and location of skin in that region, and the high vasoreactive circulation in that region. This process is typically used as a preprocessing step to find regions of the subject's skin that potentially have a robust variation for pre- and post-exposure image acquisition. For example, skin image recognition is used in multiple applications of image processing algorithms like face recognition, skin disease detection, gesture tracking and human-computer interaction. The initial parameter used for skin recognition from an image is the skin color. But color cannot be the only deciding factor due to the variation of endothelial function in pre and post exposure to different environmental internal or external stimuli. Other factors such as the light conditions also affect the results. Therefore, the skin tone is often combined with other cues like texture and edge features. This is accomplished by breaking down the computer image into individual pixels and classifying them into pre and post exposure-colored variables. One simple method is to check if each skin pixel falls into a defined color range or values in some coordinates of a color space. As stated earlier there are many color spaces like RGB, HSV, YCbCr, YIQ, YUV, etc. that are used for skin color segmentation. We have proposed a new threshold based on the combination of RGB, HSV and YCbCr values. The following factors should be considered for determining the endothelial function threshold range: 1) Effect of illumination depending on the exposure pre and post medication application; 2) Individual characteristics such as age, sex and body parts; 3) Varying endothelial function assessment with respect to different medication administered with varying doses and ranges; 4) Other factors such as background colors, shadows and motion blur. The skin detection is influenced by the parameters like Brightness, Contrast, Transparency, Illumination, and Saturation. The detection is normally optimized by taking into consideration combinations of the mentioned parameters in their ideal ranges.

Figure 7:
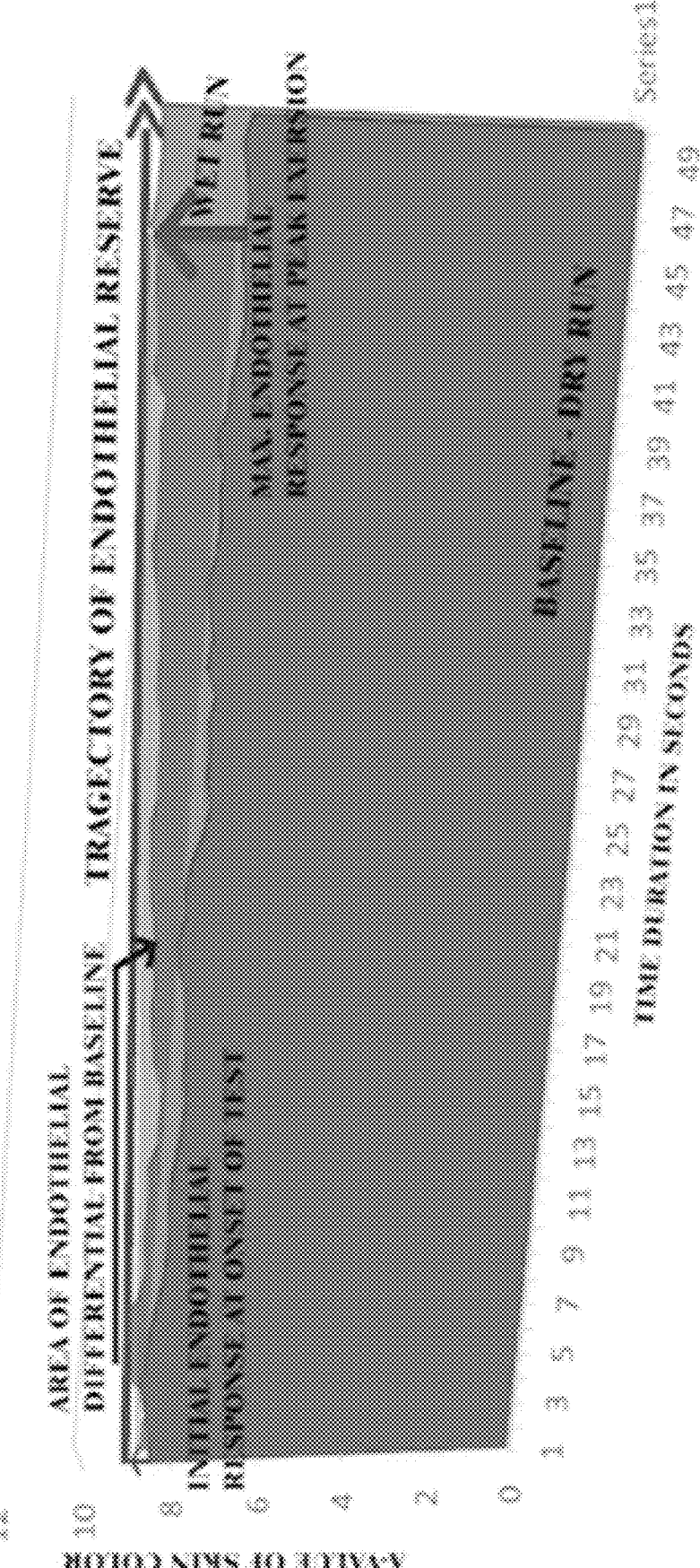
FIG. 7 is an annotated graph of results of an evaluation according to a non-limiting embodiment of the subject technology described in Example 4.
Figure 8:
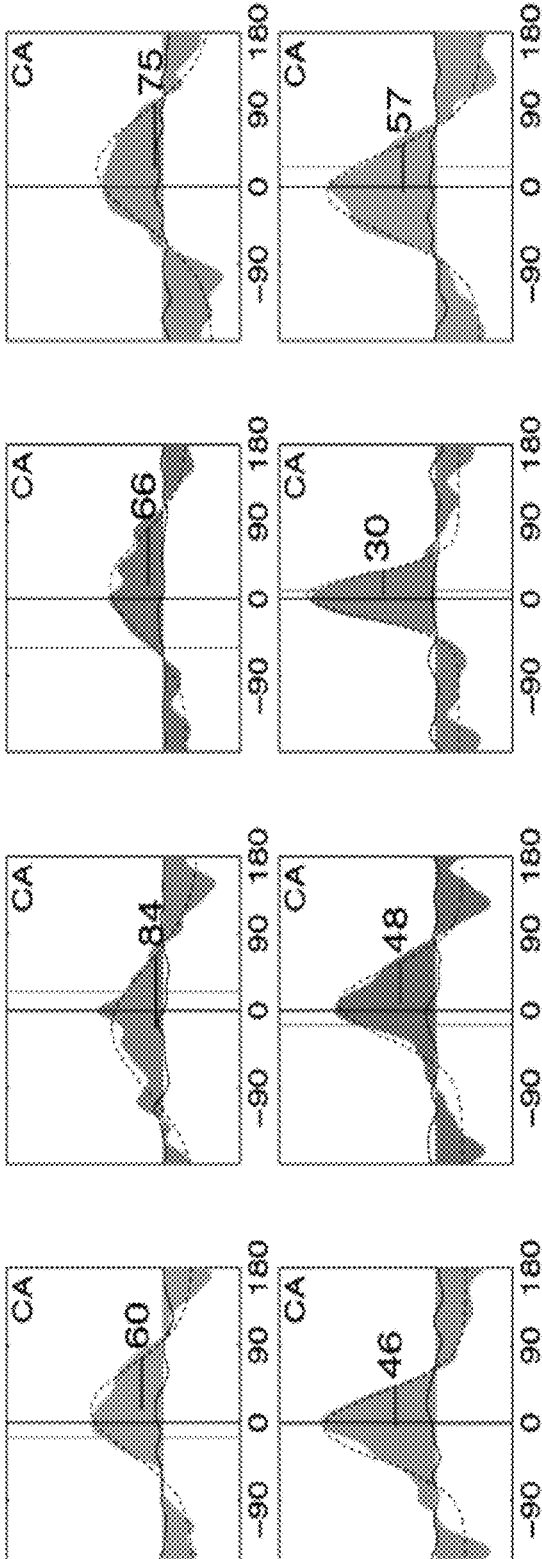
FIG. 8 is a set of color histograms representing skin color data which is captured and analyzed in an embodiment of the subject technology.

In an aspect of the subject technology, the digital color image data of the observed area of the subject's skin may be analyzed in the form of color histograms. When the digital color image data is analyzed in this way, the total area of the red color in the histograms will be calculated and compared between camera 1 ("dry run") and camera 2 ("wet run"). The difference in the area that is calculated will determine the shift in color change. For example, FIG. 7 illustrates two sets of color histograms that are a potential result of the subject technology, in which the first row of histograms represents the camera 1 "dry run" and the second row represents the camera 2 "wet run." The value of the above color area is then computed in the delta (i.e. the difference) between each corresponding color difference: camera 1 Red/camera 2 Red=A in Red Color Histogram; camera 1 Blue/camera 2 Blue=A in Blue Color Histogram; camera 1 Green/camera 2 Green=A in Green Color Histogram. The difference in A color can indicates the vasoreactivity of the change that was elicited after the control camera 1 image, and how different the vasoactive agent has changed the color responding and exhibiting a direct correlation to the response of the vascular endothelium elicited by the mechanisms caused by different stressful situation exercise, drug comparisons, exercise, lie detection fertility level and this can then allow the observing individual to make determinations of the subject's cardiovascular state and efficacy of different stimuli of exposure.

In a further aspect of the subject technology, beyond simple digital color photography of the skin surface, in embodiments of the subject invention, optical coherence tomography (OCT) is used to obtain sectional images of the subject's skin for analysis as previously described. OCT is an emerging technology for performing high-resolution cross-sectional imaging which visualizes layers of skin tissue and structures therein including blood vessels. OCT is analogous to ultrasound imaging, except that it uses light instead of sound. OCT can provide cross-sectional images of tissue structure on the micron scale in situ and in real time. As in the embodiments using color digital photography, an observed area of the subject's skin is first measured using OCT (as will be described) without application of a vasoactive substance (the "dry run"), then a vasoactive substance is applied to the observed area, and the OCT measurement is repeated with respect to the observed area (the "wet run"). The subject may be performing exercise during the runs. The results of the "dry run" and "wet run" are compared, and conclusions are drawn, as previously described.

In a run of the subject technology using OCT (whether the "dry run" or the "wet run"), the OCT technology is used to visualize and measure the vasculature and adjacent tissues directly (in a sense), rather than inferring the state of the vasculature by measuring surface skin color (which color indicates blood perfusion, which in turn is indicative of the state of the vasculature). OCT is used to take initial measurements of the epidermal skin level that would extend to a value of 0 microns to greater than 1000 microns deep in the skin. This enables measurements of the epidermal and dermal layers of the various strata of the skin, and simultaneously, measure the vasculature of the skin. Small blood vessels exist in the various strata of the skin that can be seen by the OCT machine data image acquisition. The diameter of the epidermal and subdermal vessels is thus measured and assessed very easily by either physically measuring the diameter of these small vessels on cross sectioning or long sectioning. The subject will then have the vasoactive substance applied to the observed area, and after permitting it to take effect, the same OCT image of the skin strata and small blood vessels is captured and re-evaluated to observe the effects of the vasoactive substance. In this manner, the effects of the swelling of the interstitium can then be assessed and measured in the various strata pre and post administration of the vasoactive substances. The value of the cross section and longitudinal section of those same arteries can be evaluated again using OCT after the exposure to the vasoactive substances. Again, the vasoactive substances will have inherent effects that cause vasodilation in healthy tissue and vasoconstriction in unhealthy tissue. This will allow for the evaluation of the subject's health status as well as evaluate the effects of exercise or medication administration before and after testing in therapeutic administration and implementation. The results of the size of the diameter of the vessels measured before and after vasoactive substance application can help provide additional information as to whether the implementation of the therapy is effective. The ability of these measurements to ascertain the thickness variation of the different dermatological skin strata before and after the application of the vasoactive substance can also prove to be useful and informative in being able to apply the different therapeutic interventions.

Figure 10:
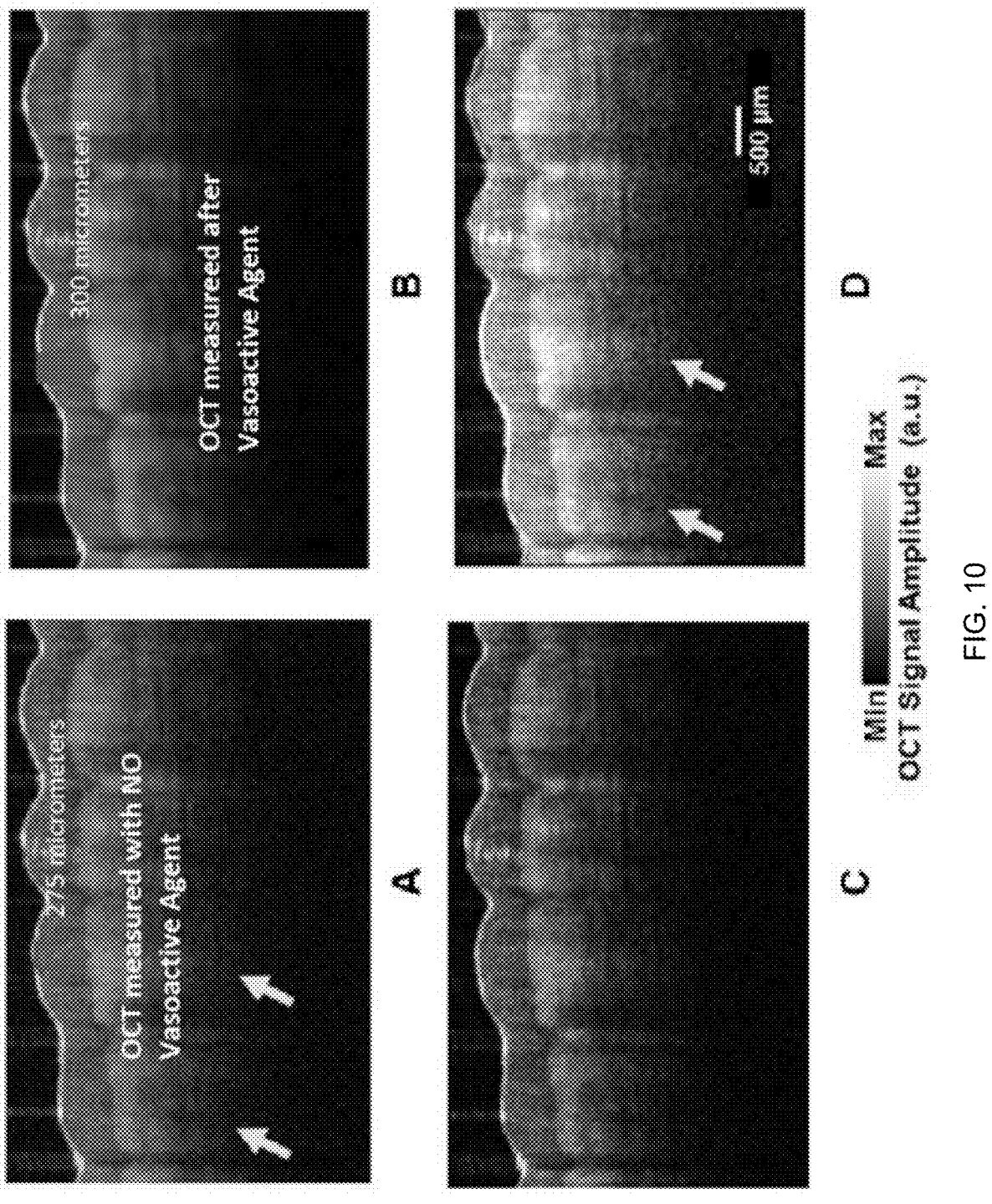
FIG. 10 is a set of annotated images of the observed area of a subject's skin taken by Optical Coherence Tomography ("OCT") which may result from an embodiment of the subject technology.

FIG. 10 shows exemplary images produced by OCT as applied in an embodiment of the subject technology. In FIG. 10, images A and C are an OCT image (annotated and not annotated, respectively) of the observed area of the subject's skin with no vasoactive agent applied (the "dry run"). Images B and D are an OCT image (annotated and not annotated, respectively) of same area of the subject's skin after application of the vasoactive agent (the "wet run"). It can be seen in these images that the thickness of the skin in the epidermis has changed due to the vasoactive substance (from 275 um to 300 um), also there are changes in the vasculature.

The same methodology can be applied using OCT algorithms that measure the difference in the thickness of the skin in the epidermis in comparing the Camera 1 measurement with no vasoactive agents and measure camera 2 measurement of the thickness of the epidermis that had the vasoactive compound applied.

The value of the above thickness is then computed in the delta difference between each corresponding OCT image between the Camera 1 with no vasoactive compound and the camera 2 with vasoactive compound. In the example of FIG. 10, camera 1 OCT reflection (275 micrometers)/camera 2 OCT reflection (300 micrometers)×100=Percentage A change in OCT Reflection.

Figure 11:
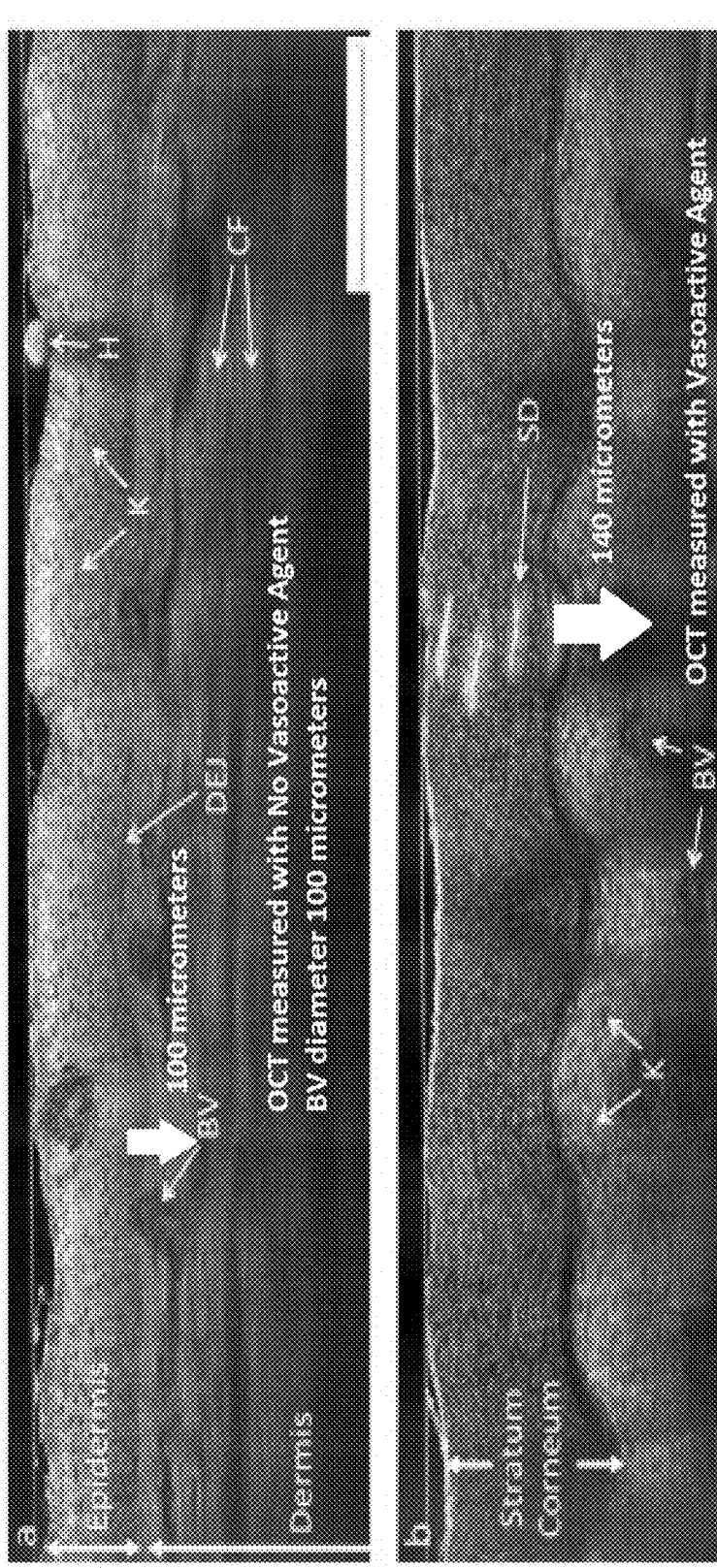
FIG. 11 is a set of annotated images of the observed area of a subject's skin taken by Optical Coherence Tomography ("OCT") which may result from an embodiment of the subject technology.

FIG. 11 shows another example of OCT images taken during application of the subject technology. Image A is an OCT image of the observed area of the subject's skin in a "dry run," while image B is the same but for the "wet run" (after application of acetylcholine). The same methodology can be applied using OCT algorithms that measure the difference in the diameter thickness of the blood vessels (BV) in the epidermis in comparing the Camera 1 measurement diameter of the BV with no vasoactive agents and measure camera 2 measurement of the diameter of the BV of the epidermis that had the vasoactive compound applied. The A difference in the measured diameter is the difference between each corresponding OCT diameter of the BV between the Camera 1 with No vasoactive compound and the camera 2 with vasoactive compound. In the example of FIG. 11, camera 1 ("dry run") OCT reflection diameter (100 micrometers)/camera 2 ("wet run") OCT reflection diameter (140 micrometers)×100=Percentage A change in OCT Reflection diameter. This will allow the observer to evaluate the change in vasoreactivity of the endothelium that is affected by different stimuli described above, be it either stress exercise, drug testing, environmental or drug induced.

In a further aspect of the subject technology, Optical Coherence Elastography (OCE) is used to measure the thickness of the elasticity of the subject skin in the observed area, in a "dry run" and a "wet run," and these measurements are used to formulate the same calculation and obtain the same type of information from the vasoactive substances described above.

The subject technology also includes using a subdermal monitoring device that can acquire photo images for colorimetric and spectrophotometric evaluation to be taken at baseline (prior to vasoactive compound exposure) and after the application of a vasoactive substance over the effective area of the device under the skin. The analysis occurs by comparing the results of the pre and post exposure data fields which create meaningful resultant curves that correspond to data collected from subjects with known illness and affect improvement confirmed over time.

Figure 12:
FIGS. 12 and 13 are renderings of an implantable color camera and associated smart device, according to a non-limiting embodiment of the subject technology.
Figure 13:
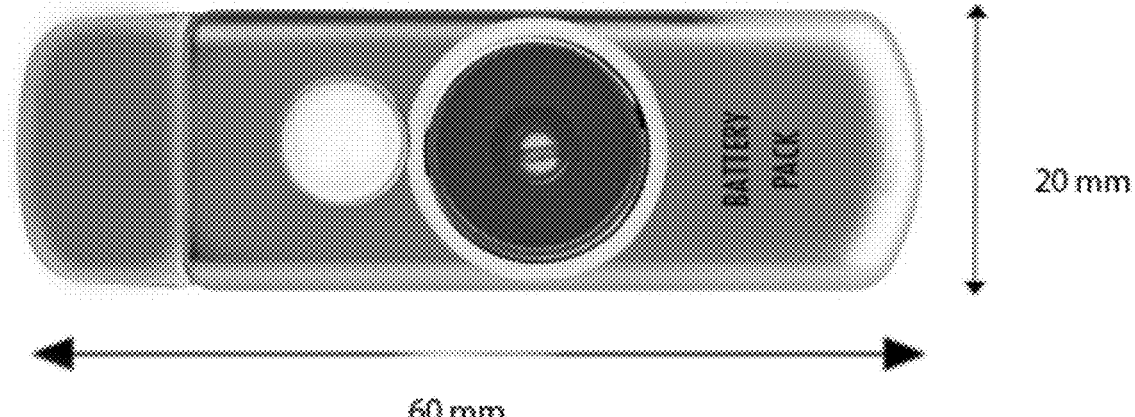
Figure 14:
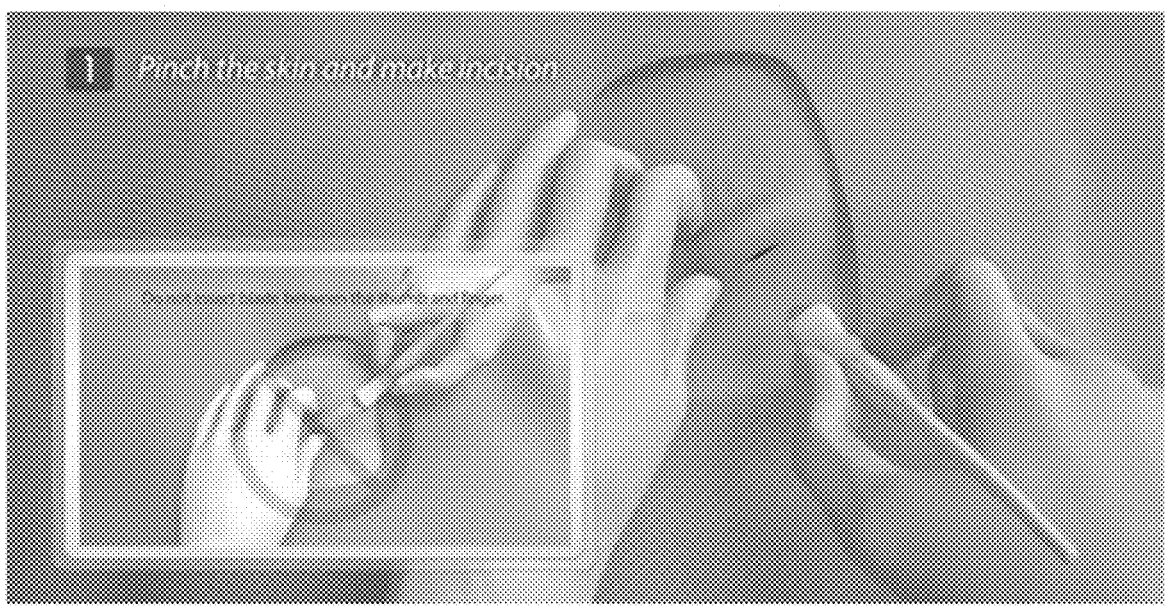
FIGS. 14-19 are renderings of surgical implantation and use of the device of FIG. 13, according to a non-limiting embodiment of the subject technology.
Figure 15:
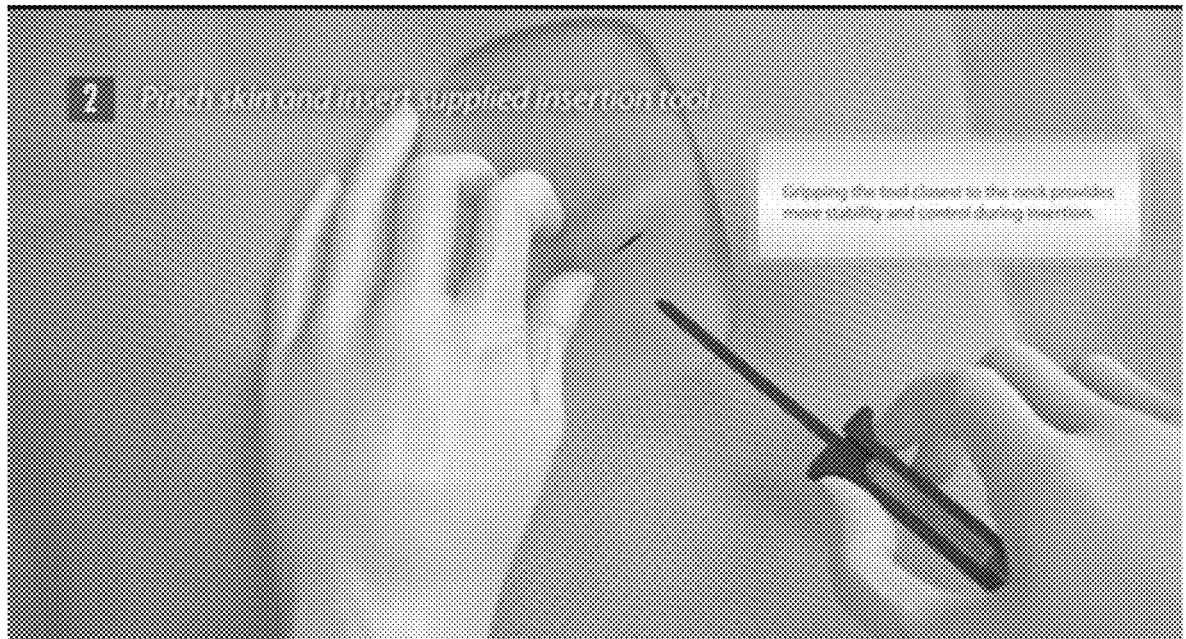
Figure 16:
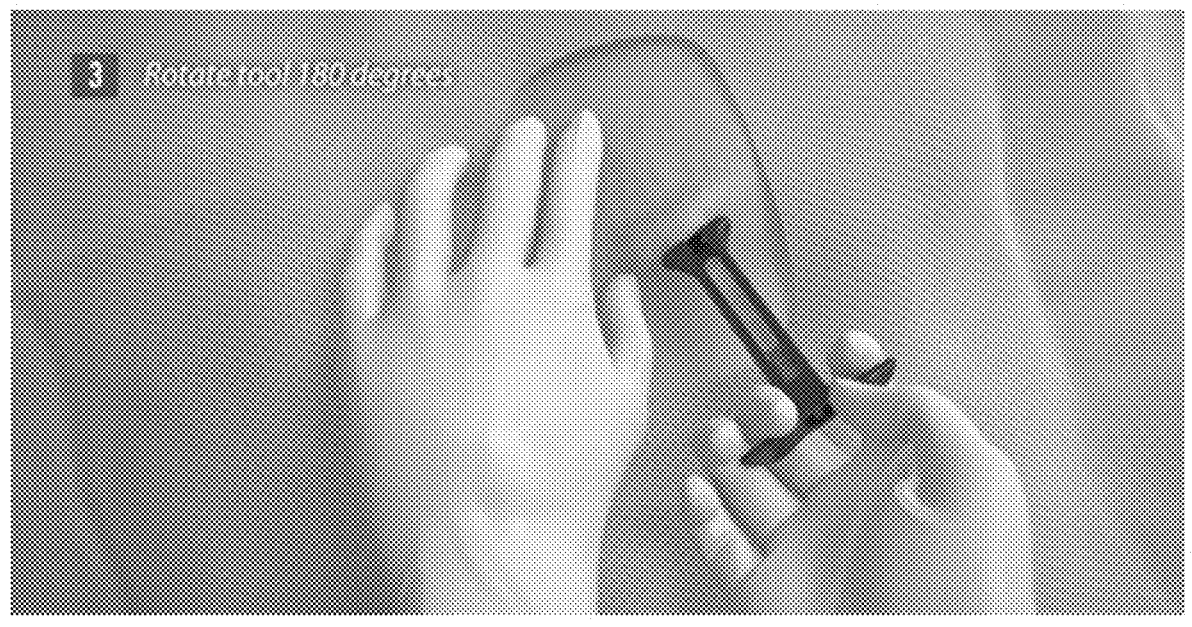
Figure 17:
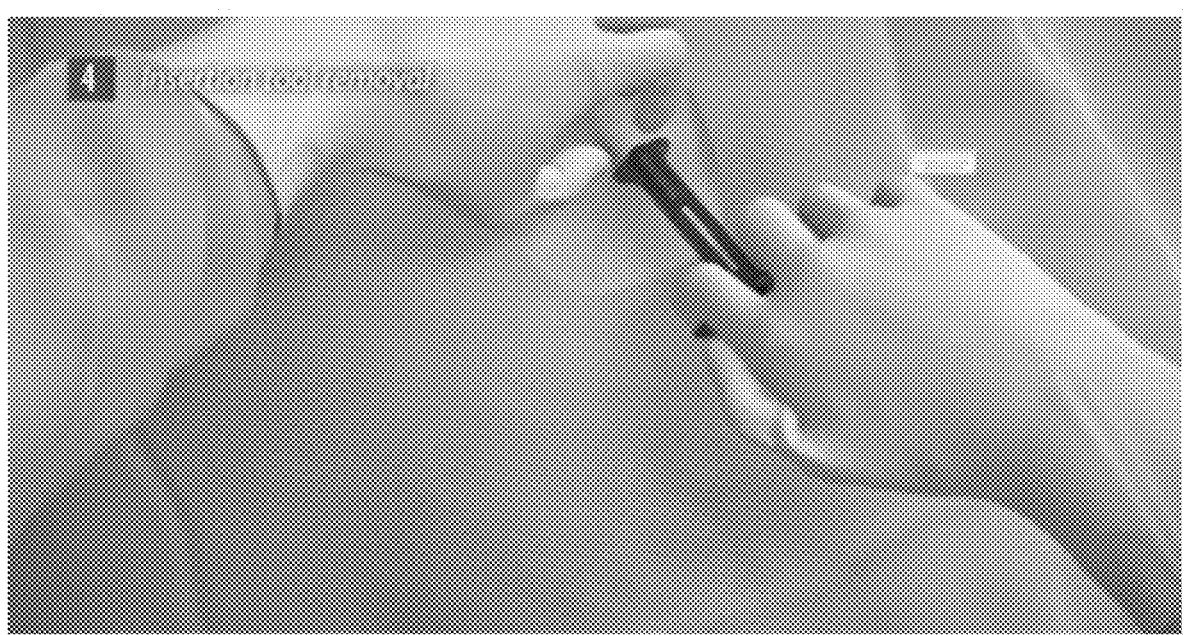
Figure 18:
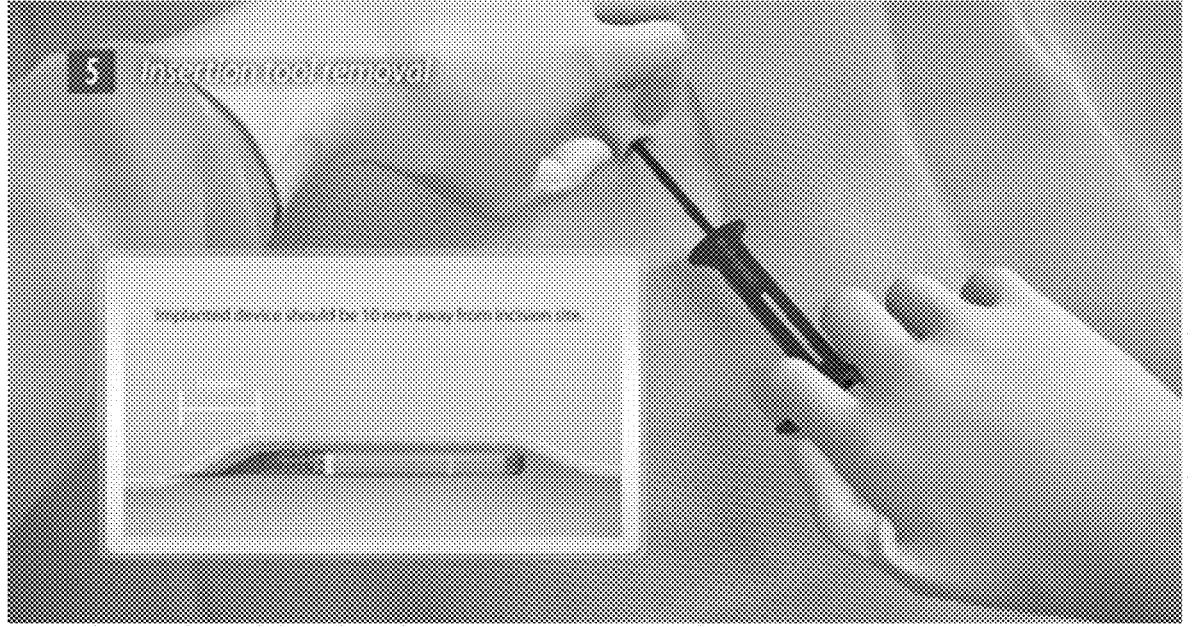

In the non-limiting embodiment of the subject technology using an implantable (subdermal), battery-powered device to gather data, as shown for example in FIG. 12-13, the implantable device has a built-in camera(s) and a light source(s) (flash) and a wireless (e.g. Bluetooth and or cellular data) transmitter that connects to a smart device such as a smart phone, or a computer, having a corresponding wireless receiver for data communication between the device and the computer, and which is also connected to the Internet.

The device is implanted in the subject's skin's interstitium in the observed area. The device may be implanted surgically, as shown for example in FIGS. 14-18. The skin is prepared for the implant site anywhere on the body using conventional antiseptic and local anesthetic procedures to maintain sterility, reduce any infection risk and minimize patient discomfort.

Figure 19:
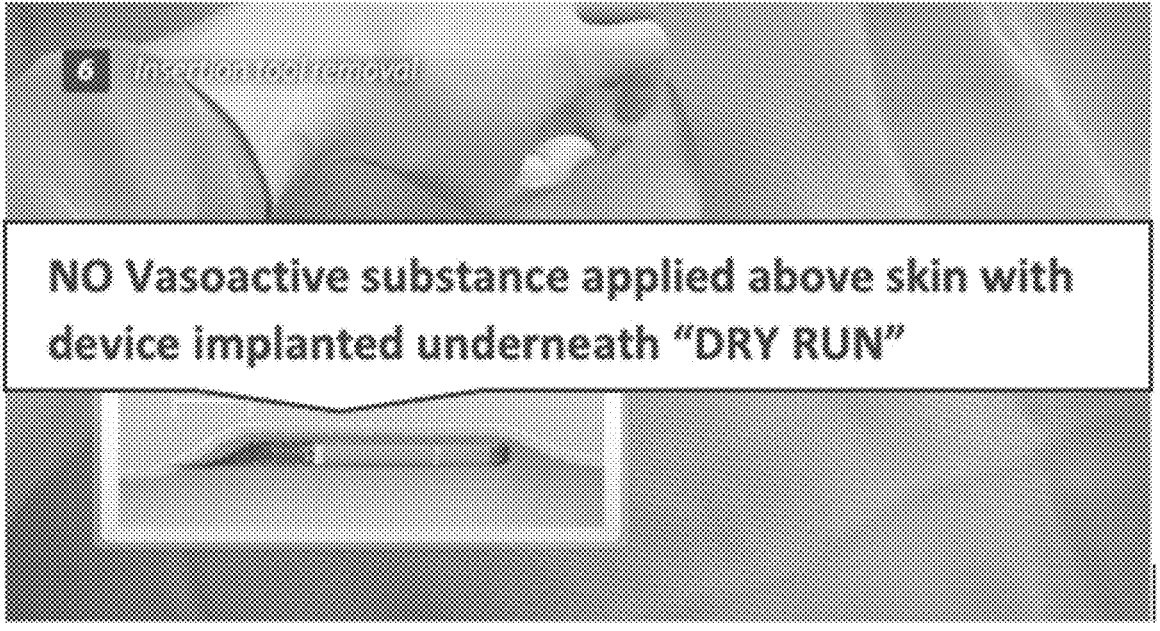
Figure 19:

The single and or multiple cameras analyze values from the visible, infrared, and/or ultraviolet light spectrums, which are indicative of the state of the vascular endothelium in the interstitium, under "dry run" followed by a "wet run" as previously described, as shown for example in FIG. 19. Custom software running on the smart device or computer will receive the information captured by the implanted device and transmitted to the computer after the testing methodology is processed on the observed area. The subject user connects the device via the wireless data link during the methodology process prescribed and the data is sent for analysis to the smart device or computer, or further, to a cloud server or other online servers, via the Internet connection.

The information that the device acquires is raw data generated by the camera and converted to digital color values resulting from vasoactive substance exposure. The data is a result of a series of digital camera scan tests which last for predetermined periods of time, and at various times during the use of the methodology, specifically before and after vasoactive substance exposure. This may be repeated on a regular basis, hours to days apart. This series of camera scan tests can be used subsequently to the onset of medical therapy use to monitor the efficacy of treatments on the vascular endothelium and interstitium in the observed area.

This aspect of the subject technology employs the highly informative nature of the endothelium and interstitium and their direct reactivity to chemical and systemic stimuli. This is key to the ability this methodology creates to evaluate with great subtlety the effect of the vasoactive chemicals on the endothelium and interstitium. The direct result is available immediately after testing and picture acquisition which will be sent either to the device i.e. smartphone or the cloud server, for example, for further processing of the information.

The dilation or constriction of the vasculature in response to stimuli is most immediately identified at capillary level, therefore, the implanted camera(s) are directed to capillary-rich regions camera. Results are available immediately after testing and cumulative testing will be most informative to obtain a well-rounded image of the vascular condition which is the first point where disease manifests. The methodology will allow for the comparison of the color value at baseline (no vasoactive substance) with the comparison of the color change in the a, b, L and spectrophotometric array of the CIE color lab system and see the difference in the same color value a,b,L and CIE lab with the application of the vasoactive substance.

The implanted device will take a picture of the interstitium that it is implanted under the skin anywhere in the body and will send the results to the device using wifi to be sent to be sent to the application or your phones cloud. The initial set of pictures will have no vasoactive substance applied to it and will be a "Dry Run" no vasoactive substances applied.

The next set of pictures from either the same camera system or a separate camera system will be taken with the application of any vasoactive substances applied over the skin above the implanted device with the camera system and will again take a similar picture of the interstitium this time after the skin has been prepared with a "Wet Run" meaning the application of a vasoactive substance. This picture will also provide us with a color value in the a,b,L and the spectrophotometric analysis or CIE lab color scheme.

The device will be able to take multiple continuous pictures at baseline and the pictures will include the color of the subcutaneous tissue without any vasoactive substance applied on the surface of the skin. It will be able to acquire the pictures either separately or in a continuous fashion to be able to be plotted on a graph to observe the changes over a time frame. The other camera on the device will be able to take the pictures after the vasoactive substance is applied over the skin to see the difference in the a,b, L shift and the spectrophotometric analysis or the color CIE lab system shift when it is compared to baseline again to be taken separate pictures or in a continuous fashion to be used to be plotted in a graph over a period of time.

The results of the above values will be taken and the difference between the two values and results obtained will be plotted and used for the difference in identification of how the endothelium response is to the vasoactive substances before and after the dry runs The delta or difference can be used to obtain the degree of differences in percentages or any other mathematical calculation between the WET and the DRY RUNS of the a, b, L, or CIE lab color schemes that can be calculated. This will allow for the observer and operator of the cloud system to evaluate these results to determine the best method in effectiveness of different stresses, physical activity, pharmacological agents that affect the body of the person that is being exposed to by the degree, and change of the a,b,L and spectrophotometric analysis or CIE lab color schemes at any particular point that the pictures are acquired.

The following non-limiting examples will illustrate embodiments and uses of the subject technology.

Example 1

Figure 2:
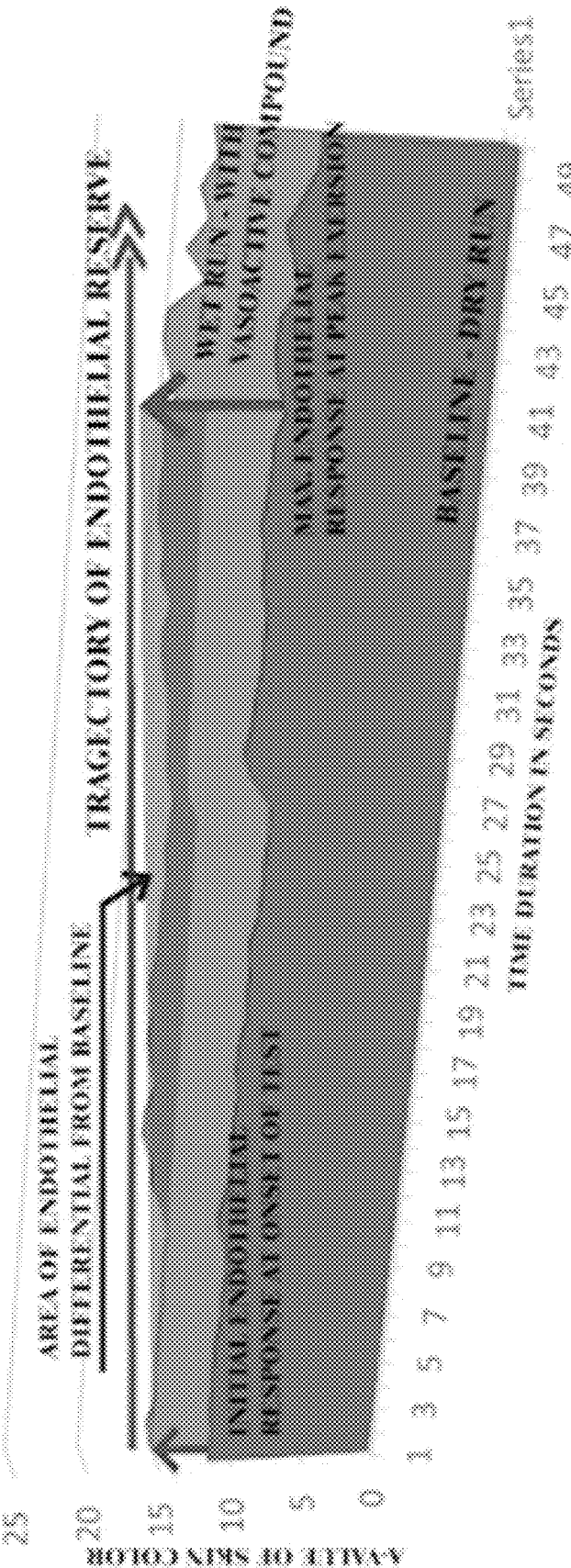
FIG. 2 is an annotated graph of results of an evaluation according to a non-limiting embodiment of the subject technology described in Example 1.

The subject is a healthy 21-year-old male. Two spectrophotomers (both Nix™ QC Color Sensors) are disposed over observed areas of the subject's skin, as in FIG. 1. Specifically, a first spectrophotomer is disposed over a dry area, and a second spectrophotomer is disposed over a "wet" treated area. In an initial "baseline dry run," the subject exercises for a period of time while skin color data is recorded from an observed area of the subject's skin. Acetylcholine is topically applied to the observed area of the subject's skin. The subject resumes exercising and a second "wet run" of skin color data is recorded from the observed area. As shown in FIG. 2, the skin color data from the "dry run" and "wet run" are graphed. The area of endothelial differential from the "wet run" over the "dry run," and the trajectory of the endothelial reserve of the "wet run" data, are indicated in FIG. 2. The result shows that the subject has a robust response to the acetylcholine and his endothelium has a good amount of reserve as the muscle strain activity enhances the response he has with exertion.

Example 2

Figure 3:
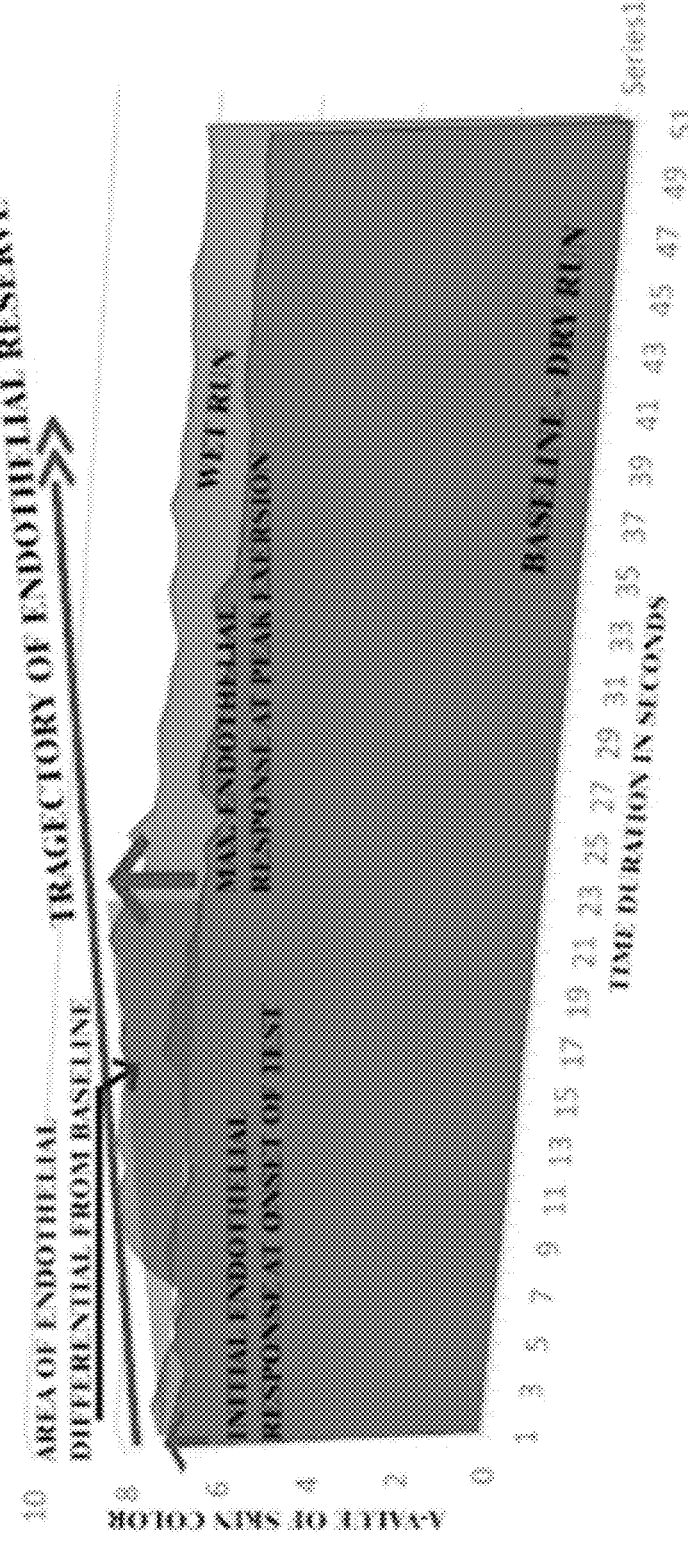
FIG. 3 is an annotated graph of results of an evaluation according to a non-limiting embodiment of the subject technology described in Example 2.
Figure 4:
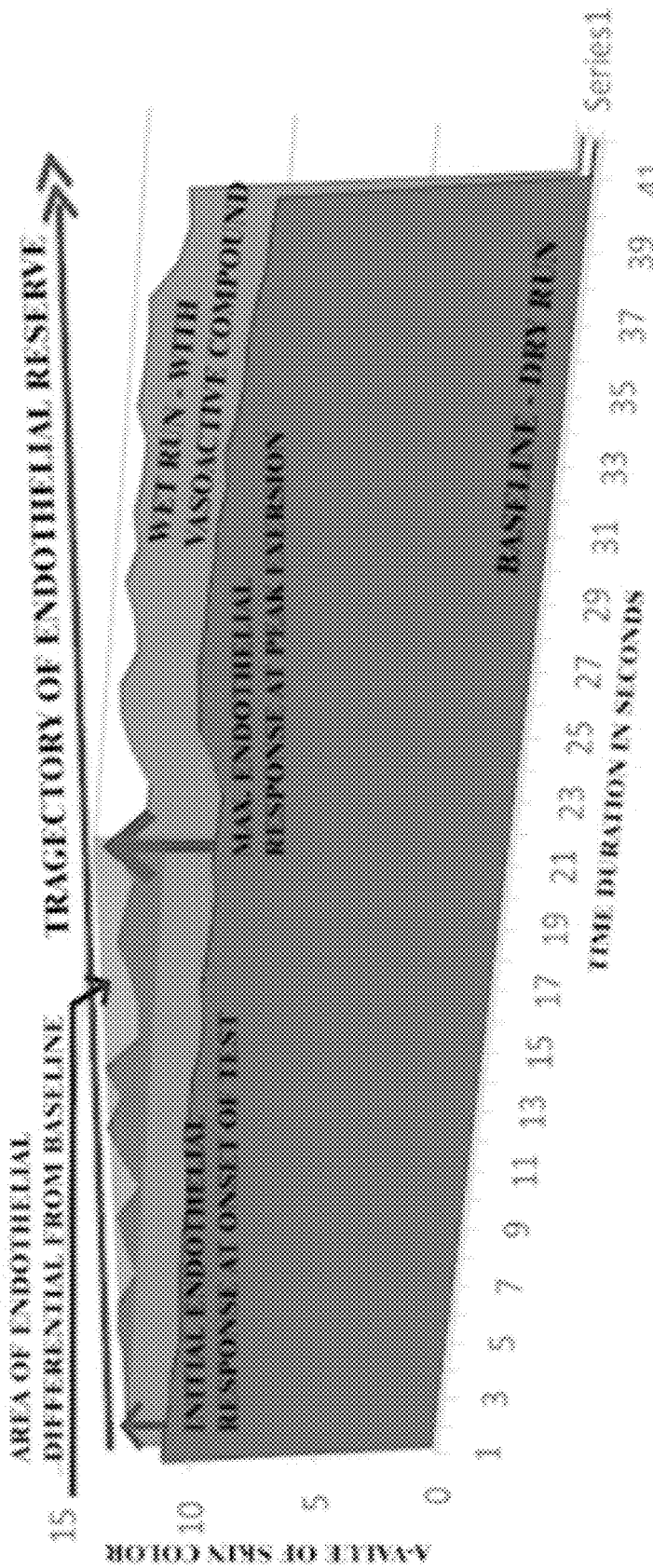
FIG. 4 is an annotated graph of results of an evaluation according to a non-limiting embodiment of the subject technology described in Example 2.

The subject is a 44-year-old female with serological evidence of hypercholesterolemia. The subject is evaluated using an embodiment of the subject technology before treatment with statins, and after a four-week use of statins (specifically Crestor®). Two spectrophotomers (both Nix™ QC Color Sensors) are disposed over observed areas of the subject's skin, as in FIG. 1. Specifically, a first spectrophotomer is disposed over a dry area, and a second spectrophotomer is disposed over a "wet" treated area. The subject performed physical exercise, specifically weightlifting, in each evaluation. As in Example 1, a "dry run" and a "wet run" (after application of acetylcholine) are performed and data collected, with the results as graphed in FIG. 3 (before statin treatment) and FIG. 4 (after four weeks of treatment). The result shows that she has a more robust response after statin use to the acetylcholine and the endothelium has a good amount of reserve as the muscle strain activity enhances the response with exertion.

Example 3

Figure 5:
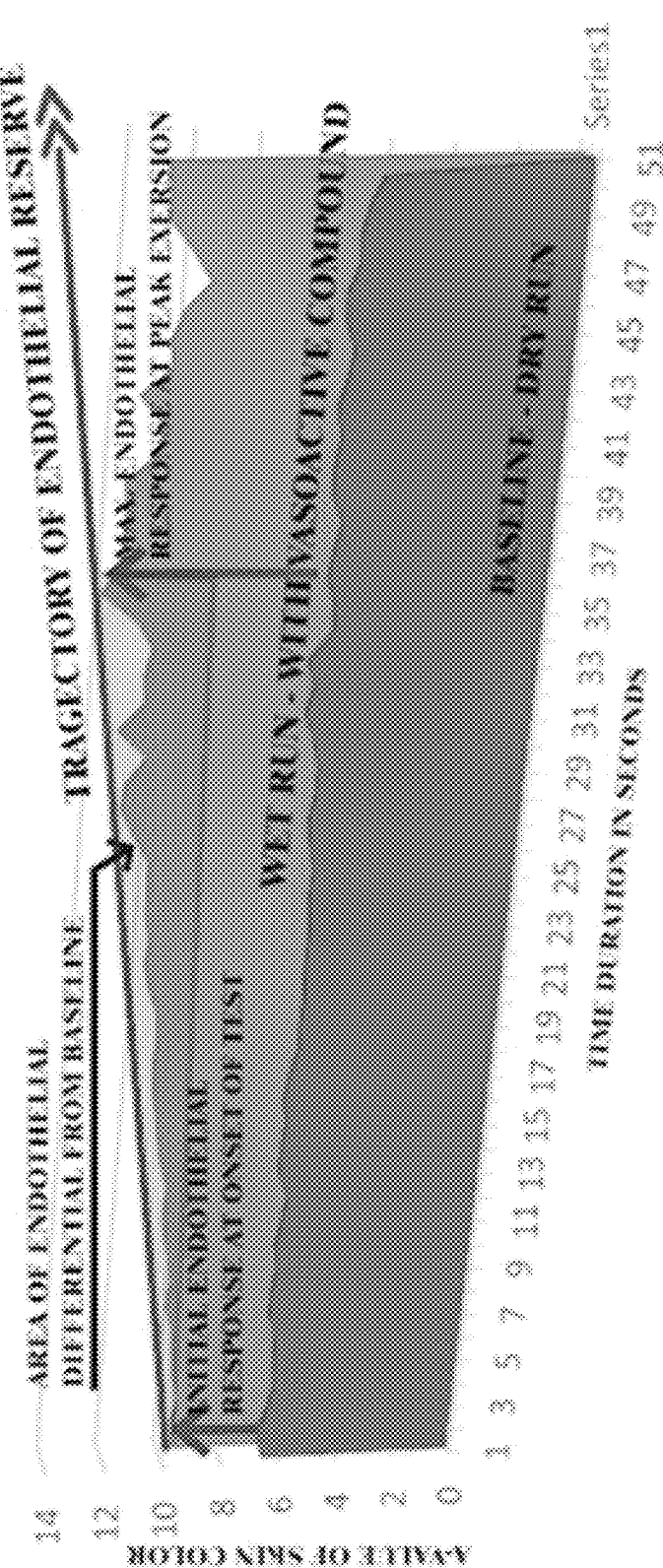
FIG. 5 is an annotated graph of results of an evaluation according to a non-limiting embodiment of the subject technology described in Example 3.

The subject is a 58-year-old male with multiple cardiac stents and bypass grafts due to diabetes and hypercholesterolemia. The subject is evaluated using an embodiment of the subject technology after treatment with Statins, Januvia and Repaatha to mitigate the endothelial effect of his various chronic conditions. Two spectrophotomers (both Nix™ QC Color Sensors) are disposed over observed areas of the subject's skin, as in FIG. 1. Specifically, a first spectrophotomer is disposed over a dry area, and a second spectrophotomer is disposed over a "wet" treated area. During the evaluation he is performing body weightlifting. As in Example 1, a "dry run" and a "wet run" (after application of acetylcholine) are performed and data collected, with the results as graphed in FIG. 5 (after treatment). The result shows preservation of endothelial function and that his medical regimen is effectively producing robust response after exposure to the acetylcholine.

Example 4

Figure 6:
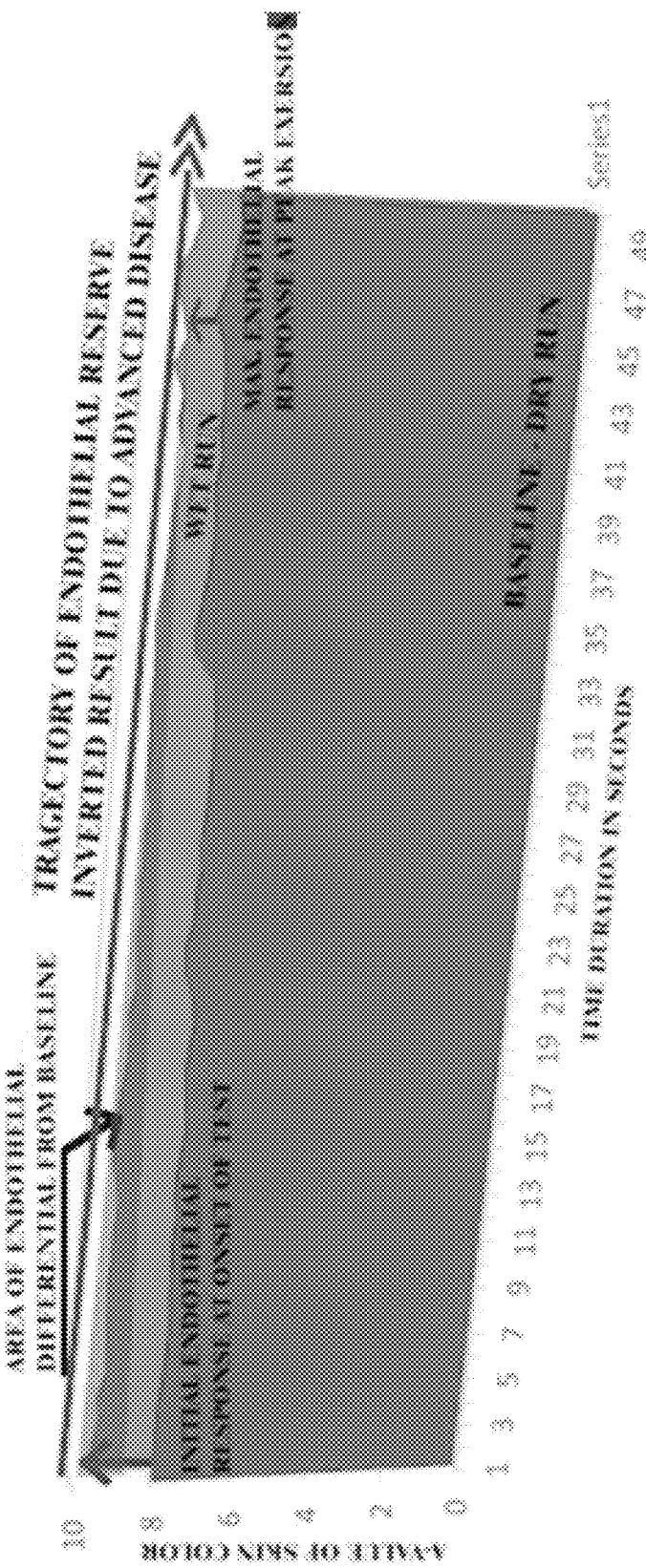
FIG. 6 is an annotated graph of results of an evaluation according to a non-limiting embodiment of the subject technology described in Example 4.

The subject is a 50-year-old female with serological evidence of hypercholesterolemia, non-obstructive cardiac disease, and history of smoking for 30+ years. The subject is evaluated using an embodiment of the subject technology before and after smoking a cigarette. Two spectrophotomers (both Nix™ QC Color Sensors) are disposed over observed areas of the subject's skin, as in FIG. 1. Specifically, a first spectrophotomer is disposed over a dry area, and a second spectrophotomer is disposed over a "wet" treated area. During the evaluation she is performing exercise. As in Example 1, a "dry run" and a "wet run" (after application of acetylcholine) are performed and data collected, with the results as graphed in FIG. 6 (before cigarette smoking) and FIG. 7 (after smoking). The results of her evaluation show the extent of endothelial dysfunction due to her chronic illnesses. FIG. 6 shows the subject's endothelium has lost its ability to produce healthy blood flow response after exertion and her a-shift, is inverted, which is expected with her medical history. FIG. 7 shows the shift after the subject smokes a cigarette which reveals a small reserve of endothelial response created by the nicotine exposure compounded with the acetylcholine which is artificially enhanced due to the stimulant. These results show that her long-term smoking has damaged the endothelium dramatically and in her case the endothelium elicit a poor enhancement when treated with vasoactive stimulants. The ability to quantify this behavior is unique to this methodology.

While specific embodiments of the subject technology have been shown and described in detail to illustrate the application of the principles of the subject technology, it will be understood that the subject technology may be embodied otherwise without departing from such principles. It will also be understood that the present subject technology includes any combination of the features and elements disclosed herein and any combination of equivalent features. The exemplary embodiments shown herein are presented for the purposes of illustration only and are not meant to limit the scope of the subject technology.

What is claimed is:

1. A method for evaluating a response of a vascular endothelium of a human subject to a stimulus, the method comprising the steps, of:

a) determining at least one baseline value of a first observed area of a subject's skin by digitally imaging a vasculature in the first observed area with a first imaging device prior to any application of a vasoactive substance in the first observed area, wherein the first imaging device is an optical coherence tomography (OCT) camera configured to obtain high-resolution cross-sectional images of the skin tissue and visualize the diameter of epidermal and subdermal blood vessels within the observed area, the first imaging device outputting at least one first digital image of at least one of an epidermal vessel or a subdermal vessel, the at least one baseline value corresponding to the at least one first digital image, wherein the at least one baseline value comprises a baseline capillary diameter;

b) applying the vasoactive substance topically to the first observed area;

c) determining at least one vasoactivated value of the first observed area by digitally imaging the vasculature in the first observed area with the first imaging device, wherein the first imaging device is further configured to measure changes in the diameter of the epidermal and subdermal vessels in response to the vasoactive substance, the first imaging device outputting at least one second digital image of at least one of the epidermal vessel or the subdermal vessel, the at least one vasoactivated value corresponding to the at least one second digital image, wherein the at least one vasoactived value comprises a vasoactivated capillary diameter;

d) comparing the at least one vasoactivated value with the at least one baseline value to determine the response of the vascular endothelium of the human subject prior to the stimulus;

e) applying the stimulus to the human subject;

f) repeating steps (a)-(c);

g) comparing the at least one vasoactivated value from step (f) with the at least one baseline value from step (f) to determine the response of the vascular endothelium of the human subject to the stimulus.

2. The method of claim 1 wherein the at least one baseline value of step (a) is a time series of baseline values and the at least one vasoactivated value of step (c) is a time series of vasoactivated values.

3. The method of claim 1 wherein the stimulus is physical exercise by the human subject.

4. The method of claim 1 wherein the stimulus is a medication administered to the human subject.

5. The method of claim 1 wherein the stimulus is a therapy administered to the human subject.

6. The method of claim 1 wherein the first imaging device is disposed on the skin of the human subject.

7. The method of claim 1 wherein the first imaging device is implanted within or beneath the skin of the human subject.

8. The method of claim 1 wherein the at least one first digital image of step (a) and the at least one second digital image of step (c) are transmitted from the first imaging device, respectively, to a computer, smart device, or cloud server.

9. A method for evaluating a response of a vascular endothelium of a human subject to a stimulus, the method comprising the steps, of:

a) determining at least one baseline value of a first observed area of a subject's skin by digitally imaging a vasculature in the first observed area with a first imaging device without any application of a vasoactive substance in the first observed area, wherein the first imaging device is an optical coherence tomography (OCT) camera configured to obtain high-resolution cross-sectional images of the skin tissue and visualize the diameter of epidermal and subdermal blood vessels within the observed area, the first imaging device outputting at least one first digital image of at least one of an epidermal vessel or a subdermal vessel, the at least one baseline value corresponding to the at least one first digital image, wherein the at least one baseline value comprises a baseline capillary diameter;

b) contemporaneously with step (a), determining at least one vasoactivated value of a second observed area to which a vasoactive substance has been topically applied, by digitally imaging vasculature in the second observed area with a second imaging device, the second imaging device being a terahertz camera, infrared camera, ultraviolet camera, optical coherence tomography (OCT) camera, or optical coherence elasticity (OCE) camera, and not a colorimeter, wherein the second imaging device is further configured to measure changes in the diameter of the epidermal and subdermal vessels in response to the vasoactive substance, the second imaging device outputting at least one second digital image of at least one of an epidermal vessel or a subdermal vessel, the at least one vasoactivated value corresponding to the at least one second digital image, wherein the at least one vasoactived value comprises a vasoactivated capillary diameter;

c) comparing the at least one vasoactivated value with the at least one baseline value to determine the response of the vascular endothelium of the human subject prior to the stimulus, d) applying the stimulus to the human subject;

e) repeating steps (a) and (b);

f) comparing the at least one vasoactivated value from step (e) with the at least one baseline value from step (e) to determine the response of the vascular endothelium of the human subject to the stimulus.

10. The method of claim 9 wherein the at least one baseline value of step (a) is a time series of baseline values and the at least one vasoactivated value of step (c) is a time series of vasoactivated values.

11. The method of claim 9 wherein the stimulus is physical exercise by the human subject.

12. The method of claim 9 wherein the stimulus is a medication administered to the human subject.

13. The method of claim 9 wherein the stimulus is a therapy administered to the human subject.

14. The method of claim 9 wherein the first imaging device or the second imaging device is implanted within or beneath the skin of the human subject.

15. The method of claim 9 wherein the at least one first digital image of step (a) and the at least one second digital image of step (b) are transmitted from the first imaging device and the second imaging device, respectively, to a computer, smart device, or cloud server.

* * * * *